US008377948B2

(12) United States Patent
Chen et al.

(10) Patent No.: US 8,377,948 B2
(45) Date of Patent: Feb. 19, 2013

(54) ANTITUMOR AGENTS AND METHODS OF THEIR USE

(75) Inventors: Ching-Shih Chen, Arlington, OH (US); Yeng-Jeng Shaw, Columbus, OH (US); Jason B. Garrison, Alexandria, VA (US); Natasha Kyprianou, Lexington, KY (US)

(73) Assignee: The Ohio State University Research Foundation, Columbus, OH (US)

( * ) Notice: Subject to any disclaimer, the term of this patent is extended or adjusted under 35 U.S.C. 154(b) by 865 days.

(21) Appl. No.: 11/570,966

(22) PCT Filed: Jun. 17, 2005

(86) PCT No.: PCT/US2005/021541
§ 371 (c)(1),
(2), (4) Date: Oct. 31, 2008

(87) PCT Pub. No.: WO2006/002088
PCT Pub. Date: Jan. 5, 2006

(65) Prior Publication Data
US 2009/0048265 A1 Feb. 19, 2009

Related U.S. Application Data

(60) Provisional application No. 60/581,649, filed on Jun. 21, 2004.

(51) Int. Cl.
*A01N 43/54* (2006.01)
*A61K 31/517* (2006.01)
*C07D 239/72* (2006.01)

(52) U.S. Cl. ..................... 514/266.1; 544/283
(58) Field of Classification Search .................. 544/283; 514/266.1
See application file for complete search history.

(56) References Cited

U.S. PATENT DOCUMENTS

| 4,341,893 A | 7/1982 | Manoury |
| 5,145,684 A | 9/1992 | Liversidge et al. |
| 6,045,829 A | 4/2000 | Liversidge et al. |

FOREIGN PATENT DOCUMENTS

| FR | 2389613 | * 12/1978 |
| WO | 01/68615 | 9/2001 |

OTHER PUBLICATIONS

Pinedo et al, "Translational Research . . . ", The Oncologist 2000; 5(suppl1); 1-2. [www.The Oncologist.com].*
McMahon, G., VEGF Receptor Signaling in Tumor Angiogenisis. The Oncologist 2000;5(suppl 1):3-10. [www.The Oncologist.com].*
Manoury et al., J' Med. Chem, 1986, vol. 19, pp. 19-25.*
Giardina et al., J. Med. Chem., 1985, vol. 28, pp. 1354-57.*
Giardina et al., J. Med. Chem., 1989, vol. 32, pp. 50-55.*
International Search Report and Written Opinion from PCT/US05/21541, mailed Mar. 29, 2006 (7 pages).

Giardina, et al., "Structure-Activity Relationships in Prazosin and WB 4101 Analogues as alpha1-Adrenoreceptor Antagonists", J Med Chem, vol. 28, No. 9, pp. 1354-1357, 1985.
Giardina, et al , "Structure-Activity Relationships in Prazosin-Related Compounds. Effect of Replacing a Piperazine Ring with an Alkanediamine Moiety on alpha1-Adrenoreceptor Blocking Activity", J Med Chem, vol. 32, No. 1, pp. 50-55, 1989.
Manoury, et al , "Synthesis and Antihypertensive Activity of a Series of 4-Amino-6,7-dimethoxyquinazoline Derivatives", J Med Chem, vol. 29, No. 1, pp. 19-25, 1986.
Anglin, et al., "Review Induction of prostate apoptosis by a1-adrenoceptor antagonists: mechanistic significance of the quinazoline component", Prostate Cancer and Prostatic Diseases, 5, pp. 89-95 (2002).
Benning et al., "Quinazoline-derived a1-Adrenoceptor Antagonists Induce Prostate Cancer Cell Apoptosis via an a 1- Andrenoceptor-independent Action", Cancer Research, 62, pp. 597-602 (2002).
Bonni et al., "Cell Survival Promoted by the Ras-MAPK Signaling Pathway by Transcription-dependent and-Independent Mechanisms", Science vol. 286, pp. 1358-1362, Nov. 12, 1999.
Cuellar, et al., "a1-Adrenoceptor Antagonists Radiosensitize Prostate Cancer Cells via Apoptosis Induction", Anticancer Research, 22, pp. 1673-1680 (2002).
Elliott, et al., "Pharmacokinetic Overview of Doxazosin", Am. J. Cardiol 59, pp. 78G-81G (1987).
Fry, David W., "Inhibition of the Epidermal Growth Factor Receptor Family of Tyrosine Kinases as an Approach to Cancer Chemotherapy: Progression from Reversible to Irreversible Inhibitors", Pharmacol. Ther., vol. 82, Nos. 2-3, pp. 207-218 (1999).
Ilio, et al., "Apoptotic Activity of Doxazosin on Prostate Stroma inVitro is Mediated Through an Autocrine Expression of TGF-B1", The Prostate, 48, pp. 131-135 (2001).
Shaw, et al., "Pharmacological Exploitation of the a1-Adrenoreceptor Antagonist Doxazosin to Develop a Novel Class of Antitumor Agents that Block Intracellular Protein Kinase B/Akt Activation", J. Med. Chem, 47, pp. 4453-4462 (2004).
Kirby, et al., "Alpha adrenoceptor blockade in the treatment of benign prostatic hyperplasia: past, present and future", British Journal of Urology, 80, pp. 521-532 (1997).
Kyprianou et al, "Suppression of human prostate cancer cell growth by a 1-Adenoceptor antagonists doxazosin and terazosin via induction of apoptosis", Cancer Research 60, pp. 4550-4555 (2000).
Kyprianou, et al., "Induction of apoptosis in the prostate by a1-Adrenoceptor antagonists: A novel effect of "Old" drugs", Curr. Urol. Rep. 1, pp. 89-96 (2000).
Kyprianou, Natasha, "Doxazosin and Terazosin Suppress Prostate Growth by Inducing Apoptosis: Clinical Significance", The Journal of Urology, vol. 169, pp. 1520-1525, Apr. 2003.
Meier, et al., "Inactivation and dephosphorylation of protein kinase Ba (PKBa) promated by hyperosmotic stress" The EMBO Journal, vol. 17, No. 24, pp. 7294-7303 (1998).
Partin, et al., "Quinazoline-based a1-adrenoceptor antagonists induce prostate cancer cell apoptosis via TGF-B signalling and 1KBa induction", British Journal of Cancer, 88, pp. 1615-1621 (2003).
Cal, et al., "Doxazosin: a new cytotoxic agent for prostate cancer?", BJU International, 85, pp. 672-675 (2000).

(Continued)

*Primary Examiner* — Paul V. Ward
(74) *Attorney, Agent, or Firm* — Tarolli, Sundheim, Covell & Tummino LLP

(57) ABSTRACT

Antitumor compounds based on the α1-adrenoceptor antagonist, doxazosin, as well as compositions and methods of use. The disclosed compounds induce apoptosis in cancer cells.

22 Claims, 6 Drawing Sheets

OTHER PUBLICATIONS

Kyprianou, et al., "Effects of Alpha1-adrenoceptor (a1-AR) Antagonists on cell proliferation and apoptosis in the prostate: Therapeutic implications in prostatic disease", The Prostate Supplement 9, pp. 42-46 (2000).
Advanced RPMI 1640 (Gibco), website accessed Feb. 12, 2012.
Anoikis—wikipedia, the free encyclopedia, Nov. 28, 2007, pp. 1-2.
Apoptosis—wikipedia, the free encyclopedia, Nov. 28, 2007, pp. 1-11.
Chon et al., "a1-adrenoceptor antagonists terazosin and doxazosin induce prostate apoptosis without affecting cell proliferation in patients with benign prostatic hyperplasia", the J. of Urology, vol. 161, pp. 2002-2008, Jun. 1999.
Datta, S.R.; Brunet, A.; Greenberg, M.E. Cellular survival: a play in three Akts. Genes Dev 1999, 13, 2905-2927.
Dick, et al., "The Role of Cancer Stem Cells in the Initiation and Propagation of Tumorigenesis", Feb. 12-15, 2008, Los Angeles, California, one page.
Doxazosin—wikipedia, the free encyclopedia, Nov. 28, 2007.
Fetal Bovine Serum (Gibco), website accessed Feb. 23, 2012.
Garrison et al., "Novel targeting of apoptosis pathways for prostate cancer therapy", Current Cancer Drug Targets, vol. 4, pp. 85-95, 2004.
Garrison et al., "Doxazosin induces apoptosis of benign and malignant prostate cells via a death receptor-mediated pathway", Cancer Research 2006, vol. 66, No. 1, Jan. 1, 2006, pp. 464-472.
Garrison, et al., "Doxazosin mediated apoptosis and the development of novel angiostatic compounds", 27 AACR Annual Meeting Apr. 1-5, 2006, Washington DC, 2 pgs.
Garrison et al., "Doxazosin mediated apoptosis and the development of novel angiostatic compounds", American Society of Androlgy, Mar./Apr. 2007, supplement, Tampa, FL.
Garrison et al., "Novel Quinazoline-based compounds impair prostate tumorigenesis by targeting tumor vascularity", Cancer Research 67: (23): Dec. 1, 2007, pp. 11344-11352.
Harris et al., "Effect of a-1 Andrenoceptor antagonist exposure on prostate cancer incidence: an observational cohort Study", The J. of Urology, vol. 178, pp. 2176-2180, Nov. 2007.
Hill, et al., Sequencing hormonal ablation and radiotherapy in prostate cancer: A molecular and therapeutic perspective (review), Oncology Reports, 9: pp. 1151-1156 (2002).
Keledjian et al., "Reduction of Human prostate tumor vascularity by the a1-Adrenoceptor antagonist Terazosin", The Prostate, 48: pp. 71-78 (2001).
Keledjian et al., "Anoikis induction by quinazoline based a1-adrenoceptor antagonists in prostate caner cells: antagonistic effect of BCL-2", The J. of Uruology, vol. 169, pp. 1150-1156, Mar. 2003.
Keledjian et al., "Doxazosin inhibits human vascular endothelial cell adhesion, migration, and invasion", J of Cellular Biochemistry, vol. 94, pp. 374-388, 2005.
Kulp, S.K.; Yang, Y.T.; Hung, C.C.; Chen, K.F.; Lai, J.P. et al. 3-phosphoinositide-dependent protein kinase-1/Akt signaling represents a major cycloozygenase-2-independent target for celecoxib in prostate cancer cells. Cancer Res 2004, 64, 1444-1451.
Kyprianou, et al., "Induction of prostate apoptosis by Doxazosin in benign prostatic hyperplasia", The J. of Urology vol. 159, pp. 1810-1815, Jun. 1998.
Manoury, et al., "Synthesis and Antihypertensive Activity of a Series of 4-Amino-6,7-dimethoxyquinazoline Derivatives", J Med Chem, vol. 29, No. 1, pp. 19-25, 1986.
Merriam-Webster's Collegiate Dictionary, Tenth Edition, p. 868, 2002.
RPMI Mediam 1640 (Gibco), website accessed Feb. 23, 2012.
Rennebeck et al., "Anoikis and survival connections in the tumor microenvironment: is there a role in prostate cancer metastasis?",Cancer Res. 2005 65: (24); pp. 11230-11235, Dec. 15, 2005.
Terazosin—wikipedia, the free encyclopedia, Nov. 28, 2007, pp. 1-2.
Yang, C.C.; Lin, H.P.; Chen, C.S.; Yang, Y.T.; Tseng, P.H. et al. Bcl-xL mediates a survival mechanism independent of the phosphoinositide 3-kinase/Akt pathway in prostate cancer cells. J Biol Chem 2003, 278, 25872-25878.

* cited by examiner

Scheme 1

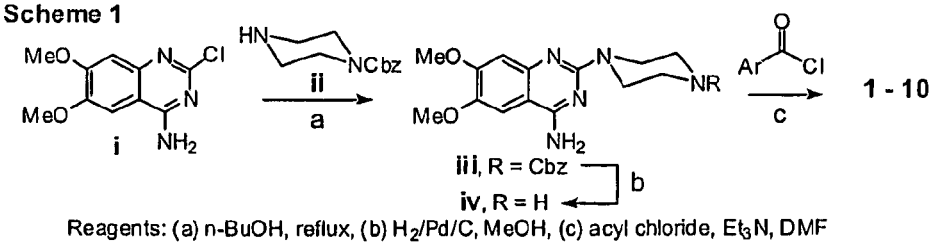

Reagents: (a) n-BuOH, reflux, (b) H₂/Pd/C, MeOH, (c) acyl chloride, Et₃N, DMF

Scheme 2

Method A

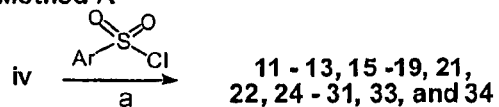

Method B

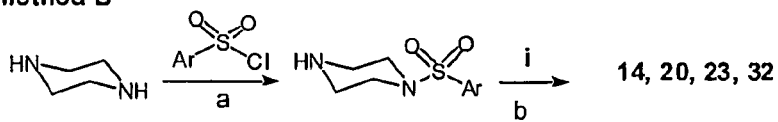

Method C

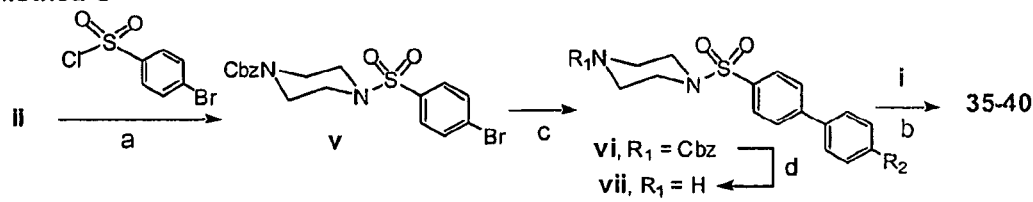

Reagents: (a) arylsulfonyl chloride, MeOH, (b) n-BuOH, reflux, (c) Suzuki coupling; arylboronic acid, Pd(OAc)₂, K₂CO₃, Bu₄NBr, H₂O, heat, (d) H₂, Pd/C, MeOH

Scheme 3

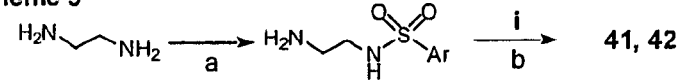

Reagents: (a) arylsulfonyl chloride, MeOH, (b) n-BuOH, reflux

Scheme 4

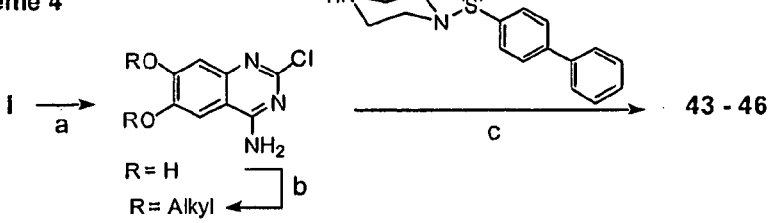

Reagents: (a) BBr₃, CH₂Cl₂, -40°C to rt, (b) alkyl bromide, K₂CO₃, MeOH, reflux, (c) n-BuOH, reflux

FIGURE 2

ANTITUMOR AGENTS AND METHODS OF THEIR USE

This application claims priority to U.S. Provisional Application No. 60/581,649, filed Jun. 21, 2004, the entire disclosure of which is incorporated herein by reference.

Work leading to this invention was supported by National Institutes of Health Grant CA94829 and Army Grant DAMD17-02-1-0117. The government has certain rights in this invention.

FIELD OF THE INVENTION

The invention relates to novel antitumor agents that act by inducing apoptosis. In some embodiments, the agents inhibit intracellular Akt activation.

BACKGROUND OF THE INVENTION

The α1-adrenoreceptor antagonist-doxazosin (CARDURA®) has been safely used for the treatment of benign prostatic hyperplasia (BPH)[1]. It relaxes prostate smooth muscle through the blockade of α1-adrenergic innervation to the prostate. In addition, this alpha-blocker also exhibits moderate potency in inducing apoptosis in prostate cancer cells[2-5], and shows synergistic antitumor effects in conjunction with radiation[6] or certain chemotherapeutics such as adriamycin and etoposide[7] against prostate cancer cells. In light of its potential use in the prevention/treatment of prostate cancer, the mechanism by which doxazosin mediates apoptosis has been the focus of many recent publications[8].

It is noteworthy that the in vitro antitumor activity of doxazosin was suggested to be mediated by an α1-adrenoreceptor-independent pathway[9]. Putative mechanisms underlying doxazosin-mediated apoptosis include the upregulation of transforming growth factor-β (TGF-β) signaling and increased gene expression of p21 and IκBα (inhibitor of NF-κB α)[10,11]. However, the apoptotic mode of action of these compounds remains unknown.

Nevertheless, from a drug discovery perspective, separation of the effect of doxazosin on apoptosis in prostate cancer cells from its original pharmacological activity in normal cells suggested that a novel class of apoptosis-inducing agents could be created through lead optimization. The present invention thus presents this novel class of apoptosis-inducing agents.

SUMMARY OF THE INVENTION

The invention is based, at least in part, on the observation that the ability of doxazosin to induce apoptotic death in PC-3 androgen-independent prostate cancer cells was, at least in part, attributable to the inhibition of intracellular Akt activation. The inventors' data suggests that the apoptosis-inducing potency of doxazosin was correlated with its efficacy in facilitating Akt dephosphorylation, and that overexpression of constitutively active Akt could partially protect cells from drug-induced apoptosis. Consequently, structural modifications of doxazosin were carried out to generate a novel class of apoptosis-inducing agents with improved efficacy in blocking intracellular Akt activation.

The present invention provides antitumor compounds having the following formula:

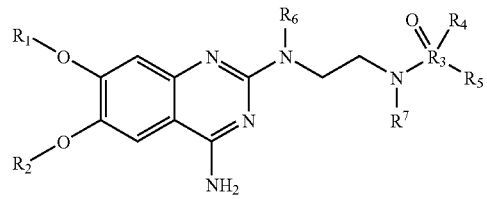

wherein:

$R_1$ and $R_2$ are the same or different and are chosen from H, alkyl, and alkenyl;

$R_3$ is chosen from C and S; wherein if $R_3$ is C, then $R_4$ is nothing and if $R_3$ is S, then $R_4$ is =O;

$R_5$ comprises an aryl group chosen from furyl, pyrrolyl, pyridyl, thiazolyl, oxazolyl, isoxazolyl, imidazolyl, pyrazolyl, pyrimidinyl, thiadiazolyl, oxadiazolyl, quinolyl, isoquinolyl, naphthyl, and phenyl, any of which may be substituted or unsubstituted; and $R_6$ and $R_7$ are i) the same or different and chosen from, H, alkyl, and alkenyl, or are ii) both —$CH_2$— and are bonded together to form a piperazinyl ring;

with the proviso that if $R_1$ and $R_2$ are both methyl, $R_3$ is C, and $R_6$ and $R_7$ are both —$CH_2$— and are bonded together to form a piperazinyl ring, then $R_5$ is not 2,3-dihydro-benzo[1,4]dioxane.

In some embodiments, $R_6$ and $R_7$ are both —$CH_2$— and are bonded together to form a piperazinyl ring. In some embodiments, $R_1$ and $R_2$ are the same and are alkyl groups, such as methyl groups. In some embodiments, $R_3$ is C and $R_5$ is chosen from 2,3-dihydrobenzo[1,4]dioxane, 4-chlorophenyl, 4-cyanophenyl, benzyloxy, 3-cyanophenyl, 4-nitrophenyl, 3,4-dimethoxyphenyl, 1-naphthyl, 4-aminophenyl, 4-t-butylphenyl, and 4-(trifluoromethyl)phenyl.

In some embodiments, $R_3$ is S, $R_4$ is =O, and $R_5$ is chosen from 4-chlorophenyl, 4-bromophenyl, 4-iodophenyl, 5-chlorothienyl, 2-nitrophenyl, 3-nitrophenyl, 4-nitrophenyl, 4-methylphenyl, 4-(trifluoromethyl)-phenyl, 4-methoxyphenyl, 4-(trifluoromethoxy)-phenyl, 4-(methylsulfonyl)-phenyl, 4-t-butylphenyl, 3-carboxyphenyl, 4-carboxyphenyl, 2,5-dichlorophenyl, 2,4-diaminophenyl, 3-carboxy-4-chloro-5-fluorophenyl, 3-carboxy-4,6-dichloro-phenyl, 1-naphthyl, 2-naphthyl, 1-(5-dimethylamino)-naphthyl, biphenyl, 2,4,6-tri-isopropyl-phenyl, and 4-(phenanthren-9-yl)phenyl.

In some embodiments, $R_5$ comprises a substituted or unsubstituted biphenyl, including but not limited to, 4'-methyl-biphenyl, 4'-trifluoromethyl-biphenyl, 4'-methylsulfonyl-biphenyl, 4'-n-butyl-biphenyl, and 4'-t-butyl-biphenyl.

In some embodiments, $R_3$ is S, $R_4$ is =O, and $R_5$ is an unsubstituted biphenyl. In some embodiments, $R_1$ and $R_2$ comprise groups chosen from methyl, ethyl, propyl, butyl, methylene, ethylene, propylene, and butylene. In some embodiments, $R_1$ and $R_2$ are the same and are chosen from allyl, n-propyl, isopropyl, and n-butyl.

In some embodiments, $R_6$ and $R_7$ are H, $R_1$ and $R_2$ are the same and are alkyl groups, such as methyl groups. In some embodiments, $R_3$ is S and $R_4$ is =O, and $R_5$ is chosen from 4-t-butyl-benzene and biphenyl.

The invention also provides compounds, wherein the compound is an ester or salt. The invention further provides pharmaceutical compositions comprising any of the compounds of the invention, and at least one pharmaceutically acceptable excipient. The invention also provides methods of inhibiting neoplastic cell proliferation in an animal, such as a human, comprising administering a therapeutically effective amount of at least one compound of the invention.

Additional features and advantages of the invention will be set forth in part in the description which follows, and in part will be obvious from the description, or may be learned by practice of the invention. The features and advantages of the invention will be realized and attained by means of the elements and combinations particularly pointed out in the appended claims.

It is to be understood that both the foregoing general description and the following detailed description are exemplary and explanatory only and are not restrictive of the invention, as claimed. The accompanying drawings, which are incorporated in and constitute a part of this specification, illustrate embodiments of the invention and together with the description, serve to explain the principles of the invention.

BRIEF DESCRIPTION OF THE DRAWINGS

FIG. 2 shows synthetic schemes employed for the structural modifications of doxazosin.

DESCRIPTION OF THE EMBODIMENTS

Figure 1:
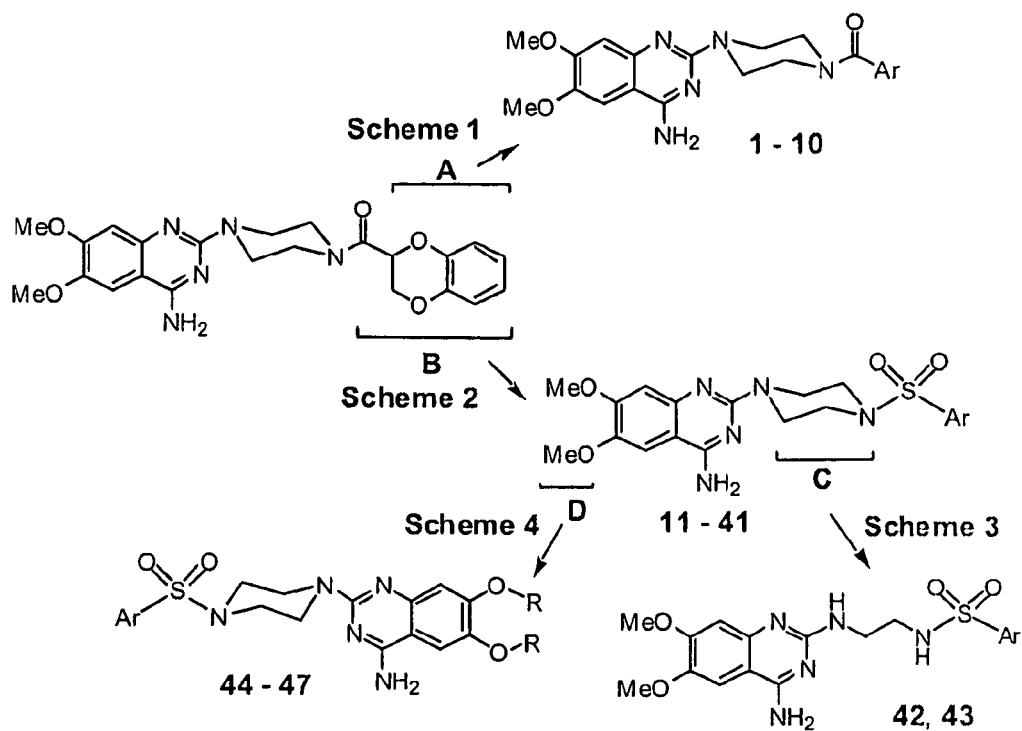
FIG. 1 schematically presents a overall strategy for the structural modification of doxazosin. A, B, C, and D denote four modification strategies that target the 2,3-dihydro-benzo[1,4]dioxane moiety, the terminal acyl function, the piperazine linker, and the methoxy side chain of the quinazoline base, respectively. The numbers indicate the designation of doxazosin derivatives.

The present invention will now be described by reference to more detailed embodiments, with occasional reference to the accompanying drawings. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are incorporated by reference in their entirety.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

Throughout this disclosure, reference will be made to compounds according to the invention. Reference to such compounds, in the specification and claims, includes esters and salts of such compounds. Thus, even if not explicitly recited, such esters and salts are contemplated, and encompassed, by reference to the compounds themselves.

As used herein, the term "hydrocarbyl" is understood to include "aliphatic," "cycloaliphatic," and "aromatic." The hydrocarbyl groups are understood to include alkyl, alkenyl, alkynyl, cycloalkyl, aryl, aralkyl, and alkaryl groups. Further, "hydrocarbyl" is understood to include both non-substituted hydrocarbyl groups, and substituted hydrocarbyl groups, with the latter referring to the hydrocarbon portion bearing additional substituents, besides carbon and hydrogen.

This invention is based, at least in part, on the discovery that the ability of doxazosin to induce apoptotic death in PC-3 androgen-independent prostate cancer cells was, at least in part, attributable to the inhibition of intracellular Akt activation. It was observed that the apoptosis-inducing potency of doxazosin is correlated with its efficacy in facilitating Akt dephosphorylation, and that overexpression of constitutively active Akt could partially protect cells from drug-induced apoptosis. Consequently, structural modifications of doxazosin were designed to generate a novel class of apoptosis-inducing agents with improved efficacy in blocking intracellular Akt activation.

The compounds of the invention have the following formula:

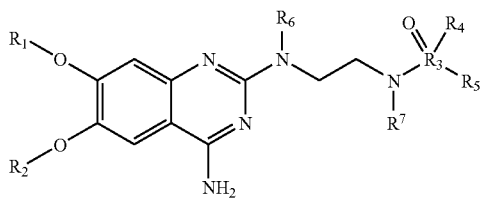

wherein:

$R_1$ and $R_2$ are the same or different and are chosen from H, alkyl, and alkenyl;

$R_3$ is chosen from C and S; wherein if $R_3$ is C, then $R_4$ is nothing and if $R_3$ is S, then $R_4$ is =O;

$R_5$ comprises an aryl group chosen from furyl, pyrrolyl, pyridyl, thiazolyl, oxazolyl, isoxazolyl, imidazolyl, pyrazolyl, pyrimidinyl, thiadiazolyl, oxadiazolyl, quinolyl, isoquinolyl, naphthyl, and phenyl, any of which may be substituted or unsubstituted; and $R_6$ and $R_7$ are i) the same or different and chosen from, H, alkyl, and alkenyl, or are ii) both —$CH_2$— and are bonded together to form a piperazinyl ring;

with the proviso that if $R_1$ and $R_2$ are both methyl, $R_3$ is C, and $R_6$ and $R_7$ are both —$CH_2$— and are bonded together to form a piperazinyl ring, then $R_5$ is not 2,3-dihydro-benzo[1,4]dioxane.

The groups $R_1$-$R_7$ are chosen from hydrocarbyl groups. Groups $R_1$ and $R_2$ can be the same or different and can be chosen from H, alkyl, and alkenyl; $R_1$ and $R_2$ can be any hydrocarbyl chain, branched or unbranched, substituted or unsubstituted with heteroatoms, having from about 1 to about 10 carbons. Examples of alkyl groups include, but are not limited to, methyl, ethyl, propyl, and butyl. Examples of alkenyl groups include, but are not limited to, methenyl, ethenyl, propenyl, and butenyl. Specific examples of $R_1$ and $R_2$ include, but are not limited to, allyl, n-propyl, isopropyl, and n-butyl. Group $R_3$ can be C or S. If $R_3$ is C, then $R_4$ is nothing. If $R_3$ is S, then $R_4$ is =O.

The group $R_5$ can comprise any aryl group, including, but not limited to, furyl, pyrrolyl, pyridyl, thiazolyl, oxazolyl, isoxazolyl, imidazolyl, pyrazolyl, pyrimidinyl, thiadiazolyl, oxadiazolyl, quinolyl, isoquinolyl, naphthyl, and phenyl, any of which may be substituted or unsubstituted. Examples of aryl-containing groups include, but are not limited to, 2,3-dihydrobenzo[1,4]dioxane, 4-chlorophenyl, 4-cyanophenyl, benzyloxy, 3-cyanophenyl, 4-nitrophenyl, 3,4-dimethoxyphenyl, 1-naphthyl, 4-aminophenyl, 4-t-butylphenyl, 4-(trifluoromethyl)phenyl, 4-bromophenyl, 4-iodophenyl, 5-chlorothienyl, 2-nitrophenyl, 3-nitrophenyl, 4-nitrophenyl, 4-methylphenyl, 4-(trifluoromethyl)-phenyl, 4-methoxyphenyl, 4-(trifluoromethoxy)-phenyl, 4-(methylsulfonyl)-phenyl, 4-t-butylphenyl, 3-carboxyphenyl, 4-carboxyphenyl, 2,5-dichlorophenyl, 2,4-diaminophenyl, 3-carboxy-4-chloro-5-fluorophenyl, 3-carboxy-4,6-dichloro-phenyl, 1-naphthyl, 2-naphthyl, 1-(5-dimethylamino)-naphthyl, biphenyl, 2,4,6-tri-isopropyl-phenyl, 4-(phenanthren-9-yl) phenyl, 4'-methyl-biphenyl, 4'-trifluoromethyl-biphenyl, 4'-methylsulfonyl-biphenyl, 4'-n-butyl-biphenyl, 4'-t-butyl-biphenyl, and 4-t-butyl-benzene.

Any of the inventive compounds, employed in the methods of the invention, can be administered orally, parenterally (IV, IM, depot-IM, SQ, and depot-SQ), sublingually, intranasally (inhalation), intrathecally, topically, or rectally. Dosage forms known to those of skill in the art are suitable for delivery of the inventive compounds employed in the methods of the invention.

Compositions are provided that contain therapeutically effective amounts of the inventive compounds employed in the methods of the invention. The compounds can be formulated into suitable pharmaceutical preparations such as tablets, capsules, or elixirs for oral administration or in sterile solutions or suspensions for parenteral administration. The compounds described herein can be formulated into pharmaceutical compositions using techniques and procedures well known in the art.

About 0.1 to 1000 mg of an inventive compound or mixture of inventive compounds employed in the methods of the invention, or a physiologically acceptable salt or ester is compounded with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage in the range indicated is obtained. The compositions can be formulated in a unit dosage form, each dosage containing from about 1 to about 500 mg, or about 10 to about 100 mg of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

To prepare compositions, one or more inventive compounds employed in the methods of the invention are mixed with a suitable pharmaceutically acceptable carrier. Upon mixing or addition of the compound(s), the resulting mixture may be a solution, suspension, emulsion, or the like. Liposomal suspensions may also be used as pharmaceutically acceptable carriers. These may be prepared according to methods known to those skilled in the art. The form of the resulting mixture depends upon a number of factors, including the intended mode of administration and the solubility of the compound in the selected carrier or vehicle. The effective concentration is sufficient for lessening or ameliorating at least one symptom of the disease, disorder, or condition treated and may be empirically determined.

Pharmaceutical carriers or vehicles suitable for administration of the compounds provided herein include any such carriers suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

Where the compounds exhibit insufficient solubility, methods for solubilizing may be used. Such methods are known and include, but are not limited to, using co-solvents such as dimethylsulfoxide (DMSO), using surfactants such as TWEEN, and dissolution in aqueous sodium bicarbonate. Derivatives of the compounds, such as salts or prodrugs, may also be used in formulating effective pharmaceutical compositions.

The concentration of the compound is effective for delivery of an amount upon administration that lessens or ameliorates at least one symptom of the disorder for which the compound is administered. Typically, the compositions are formulated for single dosage administration.

The inventive compounds employed in the methods of the invention may be prepared with carriers that protect them against rapid elimination from the body, such as time-release formulations or coatings. Such carriers include controlled release formulations, such as, but not limited to, microencapsulated delivery systems. The active compound can be included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder.

The compounds and compositions of the invention can be enclosed in multiple or single dose containers. The enclosed compounds and compositions can be provided in kits, for example, including component parts that can be assembled for use. For example, an inventive compound in lyophilized form and a suitable diluent may be provided as separated components for combination prior to use. A kit may include an inventive compound and a second therapeutic agent for co-administration. The inventive compound and second therapeutic agent may be provided as separate component parts. A kit may include a plurality of containers, each container holding one or more unit dose of the inventive compound employed in the method of the invention. The containers can be adapted for the desired mode of administration, including, but not limited to tablets, gel capsules, sustained-release capsules, and the like for oral administration; depot products, pre-filled syringes, ampoules, vials, and the like for parenteral administration; and patches, medipads, creams, and the like for topical administration.

The concentration of active inventive compound in the drug composition will depend on absorption, inactivation, and excretion rates of the active compound, the dosage schedule, and amount administered as well as other factors known to those of skill in the art.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound can be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

The active materials can also be mixed with other active materials that do not impair the desired action, or with materials that supplement the desired action. The inventive compounds can be used, for example, in combination with another antitumor agent, a hormone, a steroid, or a retinoid. The antitumor agent may be one of numerous chemotherapy agents such as an alkylating agent, an antimetabolite, a hormonal agent, an antibiotic, colchicine, a vinca alkaloid, L-asparaginase, procarbazine, hydroxyurea, mitotane, nitrosoureas or an imidazole carboxamide. Suitable agents include those agents which promote depolarization of tubulin. Examples include colchicine and vinca alkaloids, including vinblastine and vincristine.

Solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerin, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include, but are not limited to, physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers. These may be prepared according to methods known in the art.

The inventive compounds may be prepared with carriers that protect the compound against rapid elimination from the body, such as time-release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

Compounds employed in the methods of the invention may be administered enterally or parenterally. When administered orally, compounds employed in the methods of the invention can be administered in usual dosage forms for oral administration as is well known to those skilled in the art. These dosage forms include the usual solid unit dosage forms of tablets and capsules as well as liquid dosage forms such as solutions, suspensions, and elixirs. When the solid dosage forms are used, they can be of the sustained release type so that the compounds employed in the methods of the invention need to be administered only once or twice daily.

The oral dosage forms can be administered to the patient 1, 2, 3, or 4 times daily. The inventive compounds employed in the methods of the invention can be administered either three or fewer times, or even once or twice daily. Hence, the inventive compounds employed in the methods of the invention be administered in oral dosage form. Whatever oral dosage form is used, they can be designed so as to protect the compounds employed in the methods of the invention from the acidic environment of the stomach. Enteric coated tablets are well known to those skilled in the art. In addition, capsules filled with small spheres each coated to protect from the acidic stomach, are also well known to those skilled in the art.

The inventive compounds employed in the methods of the invention may also be advantageously delivered in a nanocrystal dispersion formulations. Preparation of such formulations is described, for example, in U.S. Pat. No. 5,145,684, the entire contents of which is incorporated by reference. Nanocrystalline dispersions of HIV protease inhibitors and their method of use are described in U.S. Pat. No. 6,045,829, the entire contents of which is incorporated by reference. The nanocrystalline formulations typically afford greater bioavailability of drug compounds.

The inventive compounds and methods can be used to inhibit neoplastic cell proliferation in an animal. The methods comprise administering to an animal having at least one neoplastic cell present in its body a therapeutically effective amount of at least one of the inventive compounds, in compositions as described above. The animal can be a mammal, including a domesticated mammal. The animal can be a human.

The term "neoplastic cell" is used to denote a cell that shows aberrant cell growth. The aberrant cell growth of a neoplastic cell includes increased cell growth. A neoplastic cell may be, for example, a hyperplastic cell, a cell that shows a lack of contact inhibition of growth in vitro, a benign tumor cell that is incapable of metastasis in vivo, or a cancer cell that is capable of metastases in vivo and that may recur after attempted removal. The term "tumorigenesis" is used to denote the induction of cell proliferation that leads to the development of a neoplastic growth.

The terms "therapeutically effective amount" and "therapeutically effective period of time" are used to denote treatments at dosages and for periods of time effective to reduce neoplastic cell growth. As noted above, such administration can be parenteral, oral, sublingual, transdermal, topical, intranasal, or intrarectal. When administered systemically, the therapeutic composition can be administered at a sufficient dosage to attain a blood level of the inventive compounds of from about 0.1 µM to about 100 mM. For localized administration, much lower concentrations than this can be effective, and much higher concentrations may be tolerated. One of skill in the art will appreciate that such therapeutic effect resulting in a lower effective concentration of the inventive compound may vary considerably depending on the tissue, organ, or the particular animal or patient to be treated according to the invention. It is also understood that while a patient may be started at one dose, that dose may be varied over time as the patient's condition changes.

The present invention provides compositions and methods for treating a cell proliferative disease or condition in an animal, comprising administering to an animal in need of such treatment a therapeutically effective amount of a compound of the invention. As noted, the animal can be a mammal, including a domesticated mammal. The animal can be a human.

The term "cell proliferative disease or condition" is meant to refer to any condition characterized by aberrant cell growth, preferably abnormally increased cellular proliferation. Examples of such cell proliferative diseases or conditions include, but are not limited to, cancer, restenosis, and psoriasis. In some embodiments, the invention provides a method for inhibiting neoplastic cell proliferation in an animal comprising administering to an animal having at least one neoplastic cell present in its body a therapeutically effective amount of a compound of the invention. Cancers treatable according to the invention include, but are not limited to, prostate cancer, lung cancer, acute leukemia, multiple myeloma, bladder carcinoma, renal carcinoma, breast carcinoma, colorectal carcinoma, neuroblastoma, brain cancer, ovarian cancer, or melanoma.

It should be apparent to one skilled in the art that the exact dosage and frequency of administration will depend on the particular compounds employed in the methods of the invention administered, the particular condition being treated, the severity of the condition being treated, the age, weight, general physical condition of the particular patient, and other medication the individual may be taking as is well known to administering physicians who are skilled in this art.

EXAMPLES

The following details are applicable to all Examples.
Cell Culture.
PC-3 (p53−/−) human androgen-nonresponsive prostate cancer cells were purchased from the American Type Tissue Collection (Manassas, Va.). Cells were cultured in RPMI 1640 medium (Gibco, Grand Island, N.Y.) supplemented with 10% fetal bovine serum (FBS; Gibco) at 37° C. in a humidified incubator containing 5% $CO_2$.
Cell Viability Assay.
Effect of the test agent on cell viability was assessed by the MTT {[3-(4,5-dimethylthiazol-2-yl)-2,5-diphenyl-2H-tetrazolium bromide]} assay in 96-well, flat-bottomed plates, in which 8,000 PC-3 or DU-145 cells/well were seeded. Cells were exposed to the test agent at the indicated concentrations, in six replicates, in 10% FBS-supplemented-RPMI-1640 medium at 37° C. in 5% $CO_2$ for 48 hr. The medium was removed and replaced by 150 μL of 0.5 mg/mL of MTT in RPMI-1640 medium, and cells were incubated in the CO2 incubator at 37° C. for 2 h. Supernatants were removed from the wells, and the reduced MTT dye was solubilized with 200 μL/well DMSO. Absorbance was determined on a plate reader at 570 nm.

Western Blot Analysis.

PC-3 cells (1.5×106) treated with the test agent at the indicated concentrations in RPMI 1640 medium for 24 h were collected and sonicated. Protein concentrations of the lysates were determined by using a Bradford protein assay kit (Bio-Rad, Hercules, Calif.); equivalent amounts of proteins from each lysate were resolved in 10% SDS-polyacrylamide gel and then transferred onto Immobilon-nitrocellulose membranes (Millipore, Bellerica, MA) in a semidry transfer cell. The transblotted membrane was washed twice with Tris-buffered saline (TBS) containing 0.1% Tween 20 (TBST). After blocking with TBST containing 5% nonfat milk for 40 min, the membrane was incubated with the primary antibody (1:1000 dilution) in TBST-1% nonfat milk at 4° C. overnight. After treatment with the primary antibody, the membrane was washed three times with TBST for a total of 15 min, followed by goat anti-rabbit or anti-mouse IgG-horseradish peroxidase conjugates (diluted 1:3000) for 1 h at room temperature and wash three times with TBST for a total of 1 h. The immunoblots were visualized by enhanced chemiluminescence.

Transient Transfection.

The constitutively active Akt construct HA-PKB-T308D/S473D was kindly provided by Dr. Brain Hemmings (Friedrich Miescher Institute, Basel, Switzerland). PC-3 cells were seeded into T-75 flasks (1.5×106/flask). Aliquots containing 3 μg of each plasmid or a control pcDNA3.1(+) vector in 750 μl of Opti-MEM medium (Invitrogen-Life Technologies, Inc.,) was incubated with 9 μl of the FuGene 6 reagent (Roche Diagnostics Corp., Indianapolis, Ind.) for 15 min. Each flask was washed with Opti-MEM medium and then received the plasmid-FuGene 6 mixture and 4 ml of Opti-MEM medium. The flask was placed in a $CO_2$ incubator for 4 h, and the transfection medium was replaced with 10% FBS-supplemented RPMI 1640. After 24 h, Mock-, and Akt-transfected PC-3 cells were seeded into 96-well plates at 5,000 cells/well in 10% FBS-supplemented RPMI 1640. On the next day, cells were treated in four replicate with the indicated concentrations of OSU-03012 in 1% FBS-containing medium for 24 h. MTT assay was used to determine the cell viability.

Example 1

Elucidating the Apoptotic Mechanism of Doxazosin

Figure 3:
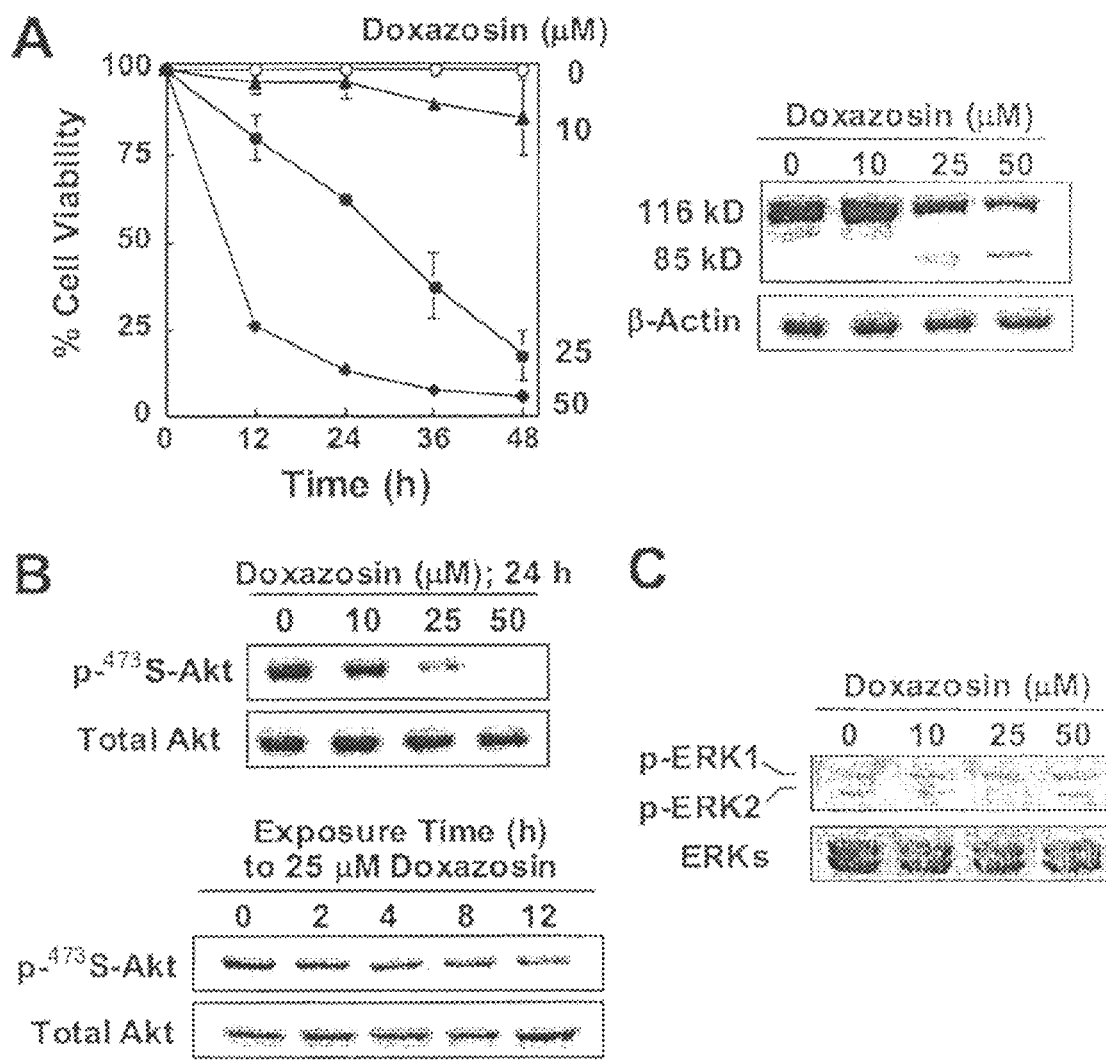
FIG. 3 shows induction of apoptosis in PC-3 cells by doxazosin. (A) Left panel, Time- and dose-dependent effect of doxazosin on the cell viability of PC-3 cells in 1% FBS-supplemented RPMI 1640 medium. Values obtained from six replicates were plotted at each time point at the indicated concentrations of doxazosin. Right panel, induction of poly (ADP-ribose) polymerase (PARP) cleavage by doxazosin at the indicated concentrations after 48-h treatment. PARP proteolysis to the apoptosis-specific 85-kd fragment was monitored by Western blotting. Although there was no substantial accumulation of the 85-kd fragment, significant decrease in the level of native protein was noted. (B) Dose- and time-dependent (upper and lower panels, respectively) effects of doxazosin on Akt phosphorylation. (C) dose-dependent effect of doxazosin on ERK phosphorylation. PC-3 cells were treated with doxazosin at the indicated concentrations for 24 h or at 25 µM for the indicated times and lysed, and proteins in the resulting supernatants were resolved on SDS-PAGE and subjected to Western blot analysis. The phosphorylation status of Akt and ERKs was determined by immunoblotting with the respective phospho-specific antibodies. Unphosphorylated Akt and ERKs, as immunostained by anti-Akt and anti-ERK antibodies, were used as internal standards for the comparison of phospho-Akt and phospho-ERK levels among samples of different preparations. The blots are representative of three independent experiments.

Doxazosin induced apoptosis, in part, by facilitating Akt dephosphorylation. Exposure of PC-3 cells to doxazosin in 1% FBS-supplemented RPMI 1640 medium resulted in a time- and dose-dependent apoptotic death, as evidenced by the disappearance of the native form of PARP (FIG. 3A). The potency of doxazosin in inducing apoptosis, however, was moderate. While PC-3 cells were susceptible to the drug-induced apoptosis at 25 μM and up, no appreciable apoptotic death was noted at 10 μM.

To shed light onto the mechanism whereby doxazosin mediated apoptosis, the effect of doxazosin on the phosphorylation state of Akt and ERKs, two signaling kinases that play a pivotal role in cell proliferation and survival[12,13], was investigated in PC-3 cells. Exposure of PC-3 cells to doxazosin caused Akt dephosphorylation in a dose- and time-dependent manner (FIG. 3B, upper and lower panel, respectively). In contrast, doxazosin, even at 50 μM, did not affect the phosphorylation status of ERKs (FIG. 3B), suggesting the specificity of the drug action on intracellular signaling pathways. It is also noteworthy that doxazosin exhibited no inhibitory effects on the kinase activity of immunoprecipitated Akt.

Figure 4:
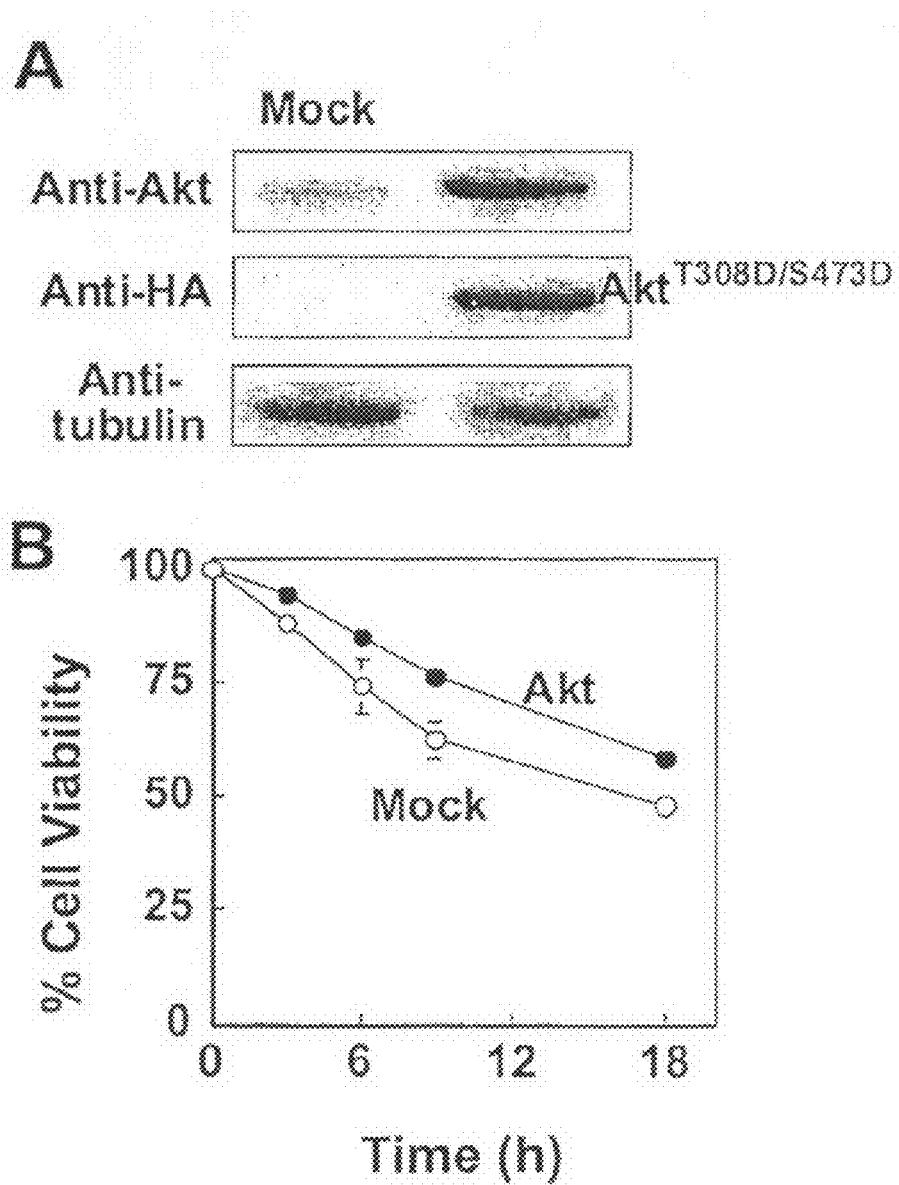
FIG. 4 shows the protective effect of constitutively active Akt on doxazosin-induced apoptotic death in PC-3 cells. (A) Expression of $Akt^{T308D/S473D}$ in PC-3 transient transfection. Western blot analysis used antibodies against Akt, and the HA tag. B) Viability of PC-3 cells overexpressing $Akt^{T308D/S473D}$ vis-à-vis cells transfected with empty pcDNA vector (mock) in the presence of 25 µM doxazosin in 1% FBS-supplemented medium for 24 h. Values are means±S.D. (n=3).

To examine the causal relationship between Akt deactivation and doxazosin-mediated apoptosis, the protective effect of the transient transfection of constitutively active Akt, $Akt^{T308D/S473D}$ (ref. 14), on drug-induced PC-3 cell death, was assessed. Western blot analysis using antibodies against Akt and the HA tag confirmed that transient transfection of $Akt^{T308D/S473D}$ led to a several-fold increase in Akt expression (FIG. 4A). These transient transfectants were exposed to 25 μM doxazosin in 1% FBS-supplemented medium to examine their susceptibility to drug-induced cell death vis-à-vis transfectants with an empty pcDNA vector (panel B). As shown, $Akt^{T308D/S473D}$ gave partial, yet significant, protection against doxazosin-induced apoptotic death.

Together, these data suggest that doxazosin-induced apoptosis in PC-3 cells was mediated, in part, through the inhibition of intracellular Akt activation. This premise was in line with the finding that the apoptosis-inducing potency of doxazosin was attenuated in 10% versus 1% FBS-supplemented medium, with $IC_{50}$ increasing from 20 μM to 45 μM. This precipitous drop in potency was reminiscent of that noted with the cyclooxygenase-2 inhibitor celecoxib[15], which might be attributable to several factors. First, like celecoxib, doxazosin displays high binding affinity with serum proteins[16], resulting in lower intracellular drug concentrations. Second, continuous stimulation of phosphoinositide 3-kinase (PI3K)/Akt signaling through various growth factor receptors counters the inhibitory effect of doxazosin on Akt. Third, serum could up-regulate Bcl-xL, which enhances the threshold to apoptotic signals emanating from PI3K/Akt inhibition[17].

Example 2

Design and Synthesis of Compounds

The results of doxazosin testing (Example 1) suggested that structural modifications could lead to improvements in the apoptotic activity. With this goal in mind, compounds were conceived, synthesized, and tested. The structural modifications were carried out in a systematic manner to increase the apoptosis-inducing activity of doxazosin. (See FIG. 1.)

Design Strategies

In Strategy A (FIG. 1), the 2,3-dihydrobenzo[1,4]dioxane moiety was replaced with different aromatic acyl-side chains to produce compounds 1-10 (FIG. 2, Scheme 1; Table 1). In Strategy B (of FIG. 1), the aryl carboxamide function was replaced with aryl sulfonamides to generate compounds 11-40 (FIG. 2, Scheme 2; Tables 2 and 3). In Strategy C (of FIG. 1), the piperazine moiety of the optimal compounds (23 and 33) was replaced by an ethylenediamine linker, generating compounds 41 and 42, respectively (FIG. 2, Scheme 3; Chart 1). In Strategy D (of FIG. 1), the methoxy side chains on the quinazoline ring of compound 33 were modified to prepare compounds 43-46 (FIG. 2, Scheme 4; Table 4).

Experimental

Chemical reagents and organic solvents were purchased from Aldrich unless otherwise mentioned. Nuclear magnetic resonance spectra ($^1$H NMR) were measured on Bruker 250 or 400 MHz. Chemical shifts (δ) are reported in parts per million (ppm) relative to TMS peak. Electrospray ionization (ESI) mass spectrometry analyses were performed with a 3-tesla Finnigan FTMS-2000 Fourier transform mass spectrometer. Elemental analyses were within ±0.4% of calculated values. Flash column chromatography was performed with silica gel (230-400 mesh). Rabbit polyclonal antibodies against Akt, phospho-Ser473-Akt, ERKs, and phospho-ERKs were purchased from New England Biolabs (Beverly, Mass.). Rabbit anti-poly(ADP-ribose) polymerase (PARP) antibodies were from BD PharMingen (San Diego, Calif.). Mouse anti-actin monoclonal antibody was from ICN Pharmaceuticals (Costa Mesa, Calif.). Goat anti-rabbit immunoglobulin G (IgG)-horseradish peroxidase conjugates were from Jackson ImmunoResearch Laboratories.

General Procedures for the Synthesis of Amides 1-10 (Scheme 1). 4-(4-Amino-6,7-dimethoxy-quinazolin-2-yl)-piperazine-1-carboxylic acid benzyl ester (iii): A mixture of 4-amino-2-chloro-6,7-dimethoxyquinazoline (2.51 g, 10 mmol) and benzyl 1-piperazine-carboxylate (2.24 g, 10 mmol) in 1-butanol (15 mL) was stirred under reflux overnight, and cooled to 80° C. The crude solid product was collected, washed with cold 1-butanol (2×10 mL), added to methanol (30 mL), and heated under reflux for 1 h. The white solid was filtered, and washed with methanol (2×10 mL) to yield compound iii. $^1$HNMR (DMSO-$d_6$) δ 3.59-3.61 (m, 4 H), 3.83-3.89 (m, 4 H), 3.85 (s, 3 H); 3.91 (s, 3 H), 5.14 (s, 2 H), 7.14 (s, 1 H), 7.34-7.88 (m, 5 H), 7.89 (s, 1 H). HRMS (M+H)$^+$ calcd for $C_{22}H_{26}N_5O_4$ 424.1979, found 424.1989. Anal. ($C_{22}H_{25}N_5O_4$.HCl) C, H, N.

[4-(4-Amino-6,7-dimethoxy-quinazolin-2-yl)-piperazin-1-yl]-(4-chloro-phenyl)-methanone (1): Compound iii (2.12 g, 5.0 mmol) was dissolved in methanol (15 mL), and 10% palladium on charcoal (20 mg, 10% w/w) and triethylamine (0.2 mL) were added. The mixture was treated with hydrogen under atmospheric pressure for 6 h, and filtered. The solvent was evaporated to obtain the intermediate 6,7-dimethoxy-2-piperazin-1-yl-quinazolin-4-ylamine (iv) without purification. $^1$HNMR (DMSO-$d_6$) δ 3.22 (br s, 4 H), 3.83 (s, 3 H), 3.87 (s, 3 H), 3.98 (br s, 4 H), 7.54 (s, 1 H), 7.69 (s, 1 H). The intermediate amine (0.578 g, 2.0 mmol) was dissolved in dry DMF (10 mL), and triethylamine (0.202 g, 2.0 mmol) was added. The resulting mixture was treated dropwise with 4-chlorobenzoyl chloride (0.35 g, 2.0 mmol) over 15 min, stirred at room temperature for 4 h, and then concentrated. The crude solid product was washed with methanol, filtered, and recrystallized from ethanol to give compound 1. $^1$HNMR (DMSO-$d_6$) δ 3.32-3.34 (m, 4 H), 3.38 (s, 3 H), 3.84 (s, 3 H), 3.77-3.88 (m, 4 H), 7.48-7.57 (m, 5 H), 7.73 (s, 1 H), 8.66 (br s, 1 H), 8.88 (br s, 1 H). HRMS (M+H)$^+$ calcd for $C_{21}H_{23}ClN_5O_3$ 428.1484, found 428.1492. Anal. ($C_{21}H_{22}ClN_5O_3$.HCl) C, H, N.

General Procedure for the Synthesis of Sulfonamides (Scheme 2). Method A. 2-[4-(4-Chloro-benzenesulfonyl)-piperazin-1-yl]-6,7-dimethoxy-quinazolin-4-yl-amine (11): To a solution of the intermediate amine iv (0.578 g, 2.0 mmol) and triethylamine (0.276 g, 2.0 mmol) in methanol (10 mL), 4-chlorobenzenesulfonyl chloride (0.443 g, 2.1 mmol) was added to the solution. The mixture was stirred at room temperature for 1 h. The resulting solid was filtered, washed with ethyl acetate (2×10 mL) to obtain the crude solid product. The crude product was stirred in methanol (10 mL) under reflux for 1 hr, filtered and dried to obtain compound 11. $^1$HNMR (DMSO-$d_6$) δ 3.27 (s, 4H), 3.35 (s, 3H), 3.85 (s, 3H), 3.99 (s, 4H), 7.55 (s, 1H), 7.60-7.80 (m, 5H), 8.63 (s, 1H), 8.80 (s, 1H). HRMS (M+H)$^+$ calcd for $C_{20}H_{23}ClN_5O_4S$ 464.1154, found 464.1158. Anal. ($C_{20}H_{22}ClN_5O_4S$.HCl) C, H, N.

Method B (14, 20, 23, 32). 2-[4-(5-Chloro-thiophene-2-sulfonyl)-piperazin-1-yl]-6,7-dimethoxy-quinazolin-4-ylamine (14): To a solution of piperazine (0.517 g, 6.0 mmol) and 5-chloro-thiophene-2-sulfonyl chloride (0.436 g, 2.0 mmol) in methanol (10 mL), the mixture was stirred at room temperature for 1 h. The solvent was evaporated, and the residue was purified with silica gel chromatography to obtain 1-(5-chloro-thiophene-2-sulfonyl)-piperazine. The intermediate (0.266 g, 1.0 mmol) and 4-amino-2-chloro-6,7-dimethoxy-quinazoline (0.251 g, 1.0 mmol) in 1-butanol (5 mL) were stirred under reflux overnight, and cooled to 80° C. The collected solid product was washed with ethyl acetate (2×10 mL), stirred in methanol (30 mL) under reflux for 1 h, filtered, washed with methanol (2×10 ml) to yield compound 14. $^1$HNMR (DMSO-$d_6$) δ 3.06-3.08 (m, 4H), 3.80 (s, 3H), 3.84 (s, 3H), 3.94 (s, 4H), 7.36 (s, 1H), 7.37 (s, 1H), 7.59 (s, 1H), 7.60 (s, 1H). HRMS (M+H)$^+$ calcd for $C_{18}H_{21}ClN_5O_4S_2$ 470.0718, found 470.0740. Anal. ($C_{18}H_{20}ClN_5O_4S_2$.HCl) C, H, N.

Method C. 6,7-Dimethoxy-2-[4-(4-phenanthren-9-yl-benzenesulfonyl)-piperazin-1-yl]-quinazolin-4-ylamine (35): To a solution of cbz-protected N-piperazine (2.24 g, 10.0 mmol) and 4-bromobenzenesulfonyl chloride (2.55 g, 10.0 mmol) in methanol (20 mL), triethylamine (1.38 g, 10.0 mmol) was added to the solution. The mixture was stirred at room temperature for 2 h, concentrated, and purified by silica gel chromatography to afford 4-(4-bromobenzenesulfonyl)-piperazine-1-carboxylic acid benzyl ester (v). Under argon, compound v (0.439 g, 1.0 mmol), $K_2CO_3$ (0.345 g, 2.5 mmol), $Bu_4NBr$ (0.322 g, 1.0 mmol) and $Pd(OAc)_2$ (11 mg, 5 mol %) were added to a stirred solution of 4-phenanthrenyl-boronic acid (0.243 g, 1.1 mmol) in $H_2O$ (5 mL). The reaction mixture was vigorously stirred at 70° C. for 1 h, cooled to room temperature, and added ethyl acetate (10 mL). The organic layer was dried and concentrated to obtain compound vi. To a solution of compound vi (0.389 g, 0.5 mmol) in methanol (5 mL), 10% palladium on charcoal (5 mg, 10% w/w) was added. The mixture was treated with hydrogen under atmospheric pressure for 6 h, and filtered. The solvent was evaporated to yield product vii. Following the procedure for the synthesis of compound 14, compound 35 was synthesized. $^1$HNMR (DMSO-$d_6$) δ 3.20 (s, 4 H), 3.81 (s, 3 H), 3.86 (s, 3 H), 3.99 (s, 4 H), 7.28 (s, 1H), 7.60-7.78 (m, 7 H), 7.81 (d, J=8.4 Hz, 2 H), 8.02 (d, J=8.1 Hz), 8.4 (s, 1 H), 8.87 (d, J=8.1 Hz, 1 H), 8.94 (d, J=8.4 Hz, 1 H). HRMS (M+H)$^+$ calcd for $C_{34}H_{32}N_5O_4S$ 606.2169, found 606.2164. Anal. ($C_{34}H_{31}N_5O_4S$.HCl) C, H, N.

General Procedure for the Synthesis of Sulfonamides (Scheme 3). N-[2-(4-Amino-6,7-dimethoxy-quinazolin-2-ylamino)-ethyl]-4-tert-butyl-benzene sulfonamide (41): A mixture of ethylenediamine (0.36 g, 6.0 mmol) and t-butyl-benzenesulfonyl chloride (0.464 g, 2.0 mmol) in methanol (15 mL) was stirred for 3 h, concentrated, and purified by silica gel chromatography to yield N-(2-amino-ethyl)-4-t-butyl-benzenesulfonamide. Following the procedure for the synthesis of compound 14, compound 42 was obtained. $^1$HNMR (DMSO-$d_6$) δ 1.17 (s, 9H), 3.11 (s, 2H), 3.48 (s, 2H), 3.86 (s, 3H), 3.93 (s, 3H), 6.90 (s, 1H), 7.50 (d, J=8.4 Hz, 2H), 7.55 (s, 1H), 7.70 (d, J=8.4 Hz, 2H). HRMS (M+H)$^+$ calcd for $C_{22}H_{30}N_5O_4S$ 460.2013, found 460.2010. Anal. ($C_{22}H_{29}N_5O_4S$.HCl) C, H, N.

General Procedure for the Synthesis of Sulfonamides (Scheme 4). 6,7-Bis-allyloxy-2-[4-(biphenyl-4-sulfonyl)-piperazin-1-yl]-quinazolin-4-ylamine (43): A solution of 4-amino-2-chloro-6,7-dimethoxyquinazoline (2.51 g, 10.0 mmol) in $CH_2Cl_2$ (30 mL) was cooled to −70° C. under argon, and added boron tribromide (6.01 g, 12.0 mmol). The mixture was allowed to warm up to room temperature over a period of 4 h, cooled to −70° C., added methanol (30 mL), and concentrated. The solid residue was washed with ethyl acetate to obtain 4-amino-2-chloro-6,7-dihydroxyquinazoline [$^1$HNMR (DMSO-$d_6$) δ 7.04 (s, 1H), 7.51 (s, 1H)]. A mixture of the first intermediate (0.21 g, 1.0 mmol), allyl bromide (0.432 g, 3.6 mmol) and $K_2CO_3$ (0.331 g, 2.4 mmol) in methanol (10 mL) was stirred under reflux for 12 h, concentrated, and purified by silica gel chromatography to afford 4-amino-2-chloro-6,7-diallyloxyquinazoline [$^1$HNMR (DMSO-$d_6$) δ 4.63 (d, J=5.4 Hz, 2H), 4.70 (d, J=1.5 Hz, 2H), 5.28 (d, J=1.3 Hz, 2H), 5.42 (d, J=1.3 Hz, 1H), 5.49 (d, J=1.3 Hz, 1H), 6.07-6.11 (m, 2H), 7.06 (s, 1H), 7.62 (s, 1H)]. A solution of the second intermediate (0.291 g, 1.0 mmol) and 1-(biphenyl-4-sulfonyl)piperazine (0.302 g, 1.0 mmol) in 1-butanol (5 mL) was stirred under reflux for 8 h, and concentrated. The solid residue was stirred with methanol under reflux for 30 min, filtered, washed with methanol to yield compound 44. $^1$HNMR (DMSO-$d_6$) δ 3.36 (br s, 4H), 4.01 (br s, 4H), 4.60-4.64 (m, 4H), 5.26-5.35 (m, 4H), 6.02-6.13 (m, 2H), 7.30-7.52 (m, 4H), 7.72-7.75 (m, 3H), 7.83-7.86 (m, 4H), 8.63 (s, 1H), 8.83 (s, 1H). HRMS (M+H)$^+$ calcd for $C_{30}H_{32}N_5O_4S$ 558.2169, found 558.2169. Anal. ($C_{30}H_{31}N_5O_4S.HCl$) C, H, N.

4-[4-(4-Amino-6,7-dimethoxy-quinazolin-2-yl)-piperazine-1-carbonyl]-benzonitrile (2): Compound 2 was synthesized from the procedure described for compound 1. $^1$HNMR (DMSO-$d_6$) δ 3.46-3.47 (m, 4H), 3.84 (s, 3H), 3.88 (s, 3H), 4.03-4.17 (m, 4H), 7.51 (s, 1H), 7.66 (d, J=8.0 Hz, 2H), 7.97 (d, J=8.0 Hz, 2H). HRMS (M+H)$^+$ calcd for $C_{22}H_{23}N_6O_3$ 419.1826, found 419.1812. Anal. ($C_{22}H_{22}N_6O_3.HCl$) C, H, N.

3-[4-(4-Amino-6,7-dimethoxy-quinazolin-2-yl)-piperazine-1-carbonyl]-benzo-nitrile (4): Compound 4 was synthesized from the procedure described for compound 1. $^1$HNMR (DMSO-$d_6$) δ 3.44-3.46 (m, 4H), 3.77 (s, 3H), 3.82 (s, 3H), 3.77-3.99 (m, 4H), 6.97 (s, 1H), 7.45 (s, 1H), 7.60-7.64 (m, 1H), 7.70-7.72 (m, 1H), 7.82-7.93 (m, 2H). HRMS (M+H)$^+$ calcd for $C_{22}H_{23}N_6O_3$ 419.1826, found 419.1823.

[4-(4-Amino-6,7-dimethoxy-quinazolin-2-yl)-piperazin-1-yl]-(4-nitro-phenyl)-methanone (5): Compound 5 was synthesized from the procedure described for compound 1. $^1$HNMR (DMSO-$d_6$) δ 3.21-3.35 (m, 4H), 3.85 (s, 3H), 3.89 (s, 3H), 3.93-3.96 (m, 4H), 7.41 (s, 1H), 7.73-7.76 (m, 3H), 7.93-8.39 (m, 2H), 8.83 (br s, 1H), 8.90 (br s, 1H). HRMS (M+H)$^+$ calcd for $C_{21}H_{23}N_6O_5$ 439.1724, found 439.1718. Anal. ($C_{21}H_{22}N_6O_5.HCl$) C, H, N.

[4-(4-Amino-6,7-dimethoxy-quinazolin-2-yl)-piperazin-1-yl]-(3,4-dimethoxy-phenyl)-methanone (6): Compound 6 was synthesized from the procedure described for compound 1. $^1$HNMR (DMSO-$d_6$) δ 3.68 (s, 4H), 3.79 (s, 3H), 3.81 (s, 3H), 3.84 (s, 3H), 3.88 (s, 3H), 4.26 (s, 4H), 7.41 (s, 1H), 7.00-7.05 (m, 3H), 7.74 (s, 1H), 8.54 (brs, 1H), 8.90 (br s, 1H). HRMS (M+H)$^+$ calcd for $C_{23}H_{28}N_5O_5$ 454.2085, found 454.2071.

[4-(4-Amino-6,7-dimethoxy-quinazolin-2-yl)-piperazin-1-yl]-naphthalen-1-yl-methanone (7): Compound 7 was synthesized from the procedure described for compound 1. $^1$HNMR (DMSO-$d_6$) δ 3.18-3.30 (m, 4H), 3.67 (s, 3H), 3.78 (s, 3H), 3.97 (br s, 2H), 4.08 (br s, 2H), 7.48 (s, 1H), 7.53-7.59 (m, 1H), 7.60-7.61 (m, 3H), 7.65 (s, 1H), 7.96 (s, 1H). HRMS (M+H)$^+$ calcd for $C_{25}H_{26}N_5O_3$ 444.2030, found 444.2030.

[4-(4-Amino-6,7-dimethoxy-quinazolin-2-yl)-piperazin-1-yl]-(4-amino-phenyl)-methanone (8): Compound 8 was synthesized from the procedure described for compound 1. $^1$HNMR (DMSO-$d_6$) δ 3.71 (s, 4H), 3.86 (s, 3H), 3.87 (s, 3H), 3.92-3.97 (m, 4H), 6.65-6.68 (m, 2H), 7.13 (d, J=3.2 Hz, 1H), 7.25 (d, J=3.4 Hz, 1H), 7.27 (d, J=3.3 Hz, 1H), 7.62 (d, J=3.2 Hz, 1H). HRMS (M+H)$^+$ calcd for $C_{21}H_{25}N_6O_3$ 409.1983, found 409.1984.

[4-(4-Amino-6,7-dimethoxy-quinazolin-2-yl)-piperazin-1-yl]-(4-tert-butyl-phenyl)-methanone (9): Compound 9 was synthesized from the procedure described for compound 1. $^1$HNMR (DMSO-$d_6$) δ 1.32 (s, 9H), 3.66-3.74 (m, 4H), 3.85 (s, 3H), 3.88 (s, 3H), 3.93 (s, 4H), 7.31-7.51 (m, 5H), 7.73 (s, 1H), 8.51 (s, 1H), 8.97 (s, 1H). HRMS (M+H)$^+$ calcd for $C_{25}H_{32}N_5O_3$ 450.2500, found 450.2485. Anal. ($C_{25}H_{31}N_5O_3.HCl$) C, H, N.

[4-(4-Amino-6,7-dimethoxy-quinazolin-2-yl)-piperazin-1-yl]-(4-trifluoromethyl-phenyl)-methanone (10): Compound 10 was synthesized from the procedure described for compound 1. $^1$HNMR (DMSO-$d_6$) δ 3.50 (s, 4H), 3.85 (s, 3H), 3.88 (s, 3H), 4.0 (s, 4H), 7.56 (s, 1H), 7.70 (d, J=7.7 Hz, 1H), 7.87 (d, J=7.7 Hz, 2H), 8.59 (s, 1H), 8.94 (s, 1H). HRMS (M+H)$^+$ calcd for $C_{22}H_{23}F_3N_5O_3$ 462.1748, found 462.1708.

2-[4-(4-Bromo-benzenesulfonyl)-piperazin-1-yl]-6,7-dimethoxy-quinazolin-4-yl-amine (12): Compound 12 was synthesized from the procedure described for compound 11. $^1$HNMR (DMSO-$d_6$) δ 3.13-3.14 (m, 4H), 3.48-3.49 (m, 4H), 3.83 (s, 3H), 3.90 (s, 3H), 6.99 (s, 1H), 7.49 (s, 1H), 7.74 (d, J=8.4 Hz, 2H), 7.83 (d, J=8.4 Hz, 2H). HRMS (M+H)$^+$ calcd for $C_{20}H_{23}BrN_5O_4S$ 508.0649, found 508.0646. Anal. ($C_{20}H_{22}BrN_5O_4S.HCl$) C, H, N.

2-[4-(4-Iodo-benzenesulfonyl)-piperazin-1-yl]-6,7-dimethoxy-quinazolin-4-yl-amine (13): Compound 13 was synthesized from the procedure described for compound II. $^1$HNMR (DMSO-$d_6$) δ 2.95 (s, 4H), 3.77 (s, 3H), 3.78-3.82 (m, 4H), 3.82 (s, 3H), 7.26-39 (m, 2H), 7.38 (d, J=8.3 Hz, 2H), 8.01 (d, J=8.5 Hz, 2H). HRMS (M+H)$^+$ calcd for $C_{20}H_{23}IN_5O_4S$ 556.0510, found 556.0496. Anal. ($C_{20}H_{22}IN_5O_4S.HCl$) C, H, N.

2-[4-(5-Chloro-thiophene-2-sulfonyl)-piperazin-1-yl]-6,7-dimethoxy-quinazolin-4-ylamine (14): Compound 14 was synthesized from the procedure described for compound 11. $^1$HNMR (DMSO-$d_6$) δ 3.06-3.08 (m, 4H), 3.80 (s, 3H), 3.84 (s, 3H), 3.94 (s, 4H), 7.36 (s, 1H), 7.37 (s, 1H), 7.59 (s, 1H), 7.60 (s, 1H). HRMS (M+H)$^+$ calcd for $C_{18}H_{21}ClN_5O_4S_2$ 470.0718, found 470.0740.

6,7-Dimethoxy-2-[4-(2-nitro-benzenesulfonyl)-piperazin-1-yl]-quinazolin-4-yl-amine (15): Compound 15 was synthesized from the procedure described for compound 11. $^1$HNMR (DMSO-$d_6$) δ 3.16 (s, 4H), 3.34 (s, 3H), 3.43 (s, 3H), 3.74 (s, 4H), 7.64 (s, 1H), 7.95 (t, J=8.1 Hz, 1H), 8.21 (d, J=7.8 Hz, 1H), 8.41 (s, 1H), 8.53 (s, 1H), 8.56 (s, 1H). HRMS (M+H)$^+$ calcd for $C_{20}H_{23}N_6O_6S$ 475.1394, found 475.1394.

6,7-Dimethoxy-2-[4-(3-nitro-benzenesulfonyl)-piperazin-1-yl]-quinazolin-4-yl-amine (16): Compound 16 was synthesized from the procedure described for compound 11. $^1$HNMR (DMSO-$d_6$) δ 3.22 (s, 4H), 3.68 (s, 3H), 3.77 (s, 3H), 3.82 (s, 4H), 6.72 (s, 1H), 7.19 (br s, 2H), 7.42 (s, 1H), 7.82-7.88 (m, 2H), 7.98-8.07 (m, 2H). HRMS (M+H)$^+$ calcd for $C_{20}H_{23}N_6O_6S$ 475.1394, found 475.1392. Anal. ($C_{20}H_{22}N_6O_6S\square HCl$) C, H, N.

6,7-Dimethoxy-2-[4-(4-nitro-benzenesulfonyl)-piperazin-1-yl]-quinazolin-4-yl-amine (17): Compound 17 was synthesized from the procedure described for compound 11. $^1$HNMR (DMSO-$d_6$) δ 3.00 (s, 4H), 3.66 (s, 3H), 3.76 (s, 3H), 3.83 (s, 4H), 6.75 (s, 1H), 7.16 (br s, 2H), 7.38 (s, 1H), 8.01 (d, J=8.6 Hz, 2H), 8.20 (d, J=8.5 Hz, 2H). HRMS (M+H)$^+$ calcd for $C_{20}H_{23}N_6O_6S$ 475.1394, found 475.1379.

6,7-Dimethoxy-2-[4-(toluene-4-sulfonyl)-piperazin-1-yl]-quinazolin-4-ylamine (18): Compound 18 was synthesized from the procedure described for compound 11. $^1$HNMR (DMSO-$d_6$) δ 29 (s, 3H), 3.03-3.07 (m, 4H), 3.82 (s, 3H), 3.85 (s, 3H), 3.98-4.05 (m, 4H), 7.45 (d, J=7.6 Hz, 2H), 7.52 (s, 1H), 7.65 (d, J=7.3 Hz, 2H), 7.73 (s, 1H), 8.55 (s, 1H), 8.92 (s, 1H). HRMS (M+H)$^+$ calcd for $C_{21}H_{26}N_5O_4S$ 444.1700, found 444.1706. Anal. ($C_{21}H_{25}N_5O_4S$·HCl) C, H, N.

6,7-Dimethoxy-2-[4-(4-trifluoromethyl-benzenesulfonyl)-piperazin-1-yl]-quinazolin-4-yl-amine (19): Compound 19 was synthesized from the procedure described for compound 11. $^1$HNMR (DMSO-d$_6$) δ 3.08 (s, 4H), 3.79 (s, 3H), 3.84 (s, 3H), 3.90 (s, 4H), 7.56 (s, 1H), 7.80-8.03 (m, 5H). HRMS (M+H)$^+$ calcd for $C_{21}H_{23}F_3N_5O_3S$ 498.1417, found 498.1420. Anal. ($C_{21}H_{22}F_3N_5O_3S$·HCl) C, H, N.

6,7-Dimethoxy-2-[4-(4-methoxy-benzenesulfonyl)-piperazin-1-yl]-quinazolin-4-yl-amine (20): Compound 20 was synthesized from the procedure described for compound 14. $^1$HNMR (DMSO-d$_6$) δ 2.95-2.97 (m, 4 H), 3.73 (s, 3 H), 3.75 (s, 3 H), 3.82 (s, 3 H), 3.73-3.82 (m, 4 H), 6.98 (s, 1 H), 7.06 (d, J=21.1 Hz, 2 H), 7.57 (d, J=19.1 Hz, 2 H). HRMS (M+H)$^+$ calcd for $C_{21}H_{26}N_5O_5S$ 460.1649, found 460.1652. Anal. ($C_{21}H_{25}N_5O_5S$·HCl) C, H, N.

6,7-Dimethoxy-2-[4-(4-trifluoromethoxy-benzenesulfonyl)-piperazin-1-yl]-quinazolin-4-yl-amine (21): Compound 21 was synthesized from the procedure described for compound 11. $^1$HNMR (DMSO-d$_6$) δ 3.40 (s, 4H), 3.66 (s, 3H), 3.69 (s, 3H), 3.71 (s, 4H), 6.68 (s, 1H), 7.00 (br s, 2H), 7.23 (s, 1H), 7.54-755 (m, 2H), 7.86-7.88 (m, 2H). HRMS (M+H)$^+$ calcd for $C_{21}H_{23}F_3N_5O_5S$ 514.1367, found 514.1363. Anal. ($C_{21}H_{22}F_3N_5O_5S$·HCl) C, H, N.

2-[4-(4-Methanesulfonyl-benzenesulfonyl)-piperazin-1-yl]-6,7-dimethoxy-quinazolin-4-ylamine (22): Compound 22 was synthesized from the procedure described for compound 11. $^1$HNMR (DMSO-d$_6$) δ 3.00 (s, 4H), 3.21 (s, 3H), 3.76 (s, 3H), 3.80 (s, 3H), 3.82 (s, 4H), 6.69 (s, 1H), 7.07 (br s, 2H), 7.26 (s, 1H), 8.01 (d, J=8.3 Hz, 2H), 8.16 (d, J=8.4 Hz, 2H). HRMS (M+H)$^+$ calcd for $C_{21}H_{26}N_5O_6S_2$ 508.1319, found 508.1317. Anal. ($C_{21}H_{25}N_5O_6S_2$·HCl) C, H, N.

2-[4-(4-tert-Butyl-benzenesulfonyl)-piperazin-1-yl]-6,7-dimethoxy-quinazolin-4-ylamine (23): Compound 23 was synthesized from the procedure described for compound 14. $^1$HNMR (DMSO-d$_6$) δ 1.28 (s, 9H), 2.90 (s, 4H), 3.76 (s, 3H), 3.80 (s, 3H), 3.90-3.98 (m, 4H), 6.70 (s, 3H), 7.17 (br s, 1H), 7.26 (s, 1H), 7.45-7.68 (m, 3H). HRMS (M+H)$^+$ calcd for $C_{24}H_{32}N_5O_4S$ 486.2170, found 486.2173. Anal. ($C_{24}H_{31}N_5O_4S$·HCl) C, H, N.

3-[4-(4-Amino-6,7-dimethoxy-quinazolin-2-yl)-piperazine-1-sulfonyl]-benzoic acid (24): Compound 24 was synthesized from the procedure described for compound 11. $^1$HNMR (DMSO-d$_6$) δ 2.99 (s, 4H), 3.77 (s, 3H), 3.82 (s, 7H), 6.78 (s, 1H), 7.38 (br s, 1H), 7.44 (s, 1H), 7.78 (t, J=7.6 Hz, 1H), 8.00 (d, J=7.4 Hz, 1H), 8.21-8.23 (m, 2H). HRMS (M+H)$^+$ calcd for $C_{21}H_{24}N_5O_6S$ 474.1442, found 474.1426.

[4-(4-Amino-6,7-dimethoxy-quinazolin-2-yl)-piperazin-1-yl]-(4-trifluoromethyl-phenyl)-methanone (25): Compound 25 was synthesized from the procedure described for compound 11. $^1$HNMR (DMSO-d$_6$) δ 3.34 (br s, 4H), 3.77 (s, 3H), 3.82 (s, 3H), 3.95 (s, 4H), 6.83 (s, 1H), 7.41-7.51 (br s, 2H), 7.66-7.71 (m, 2H), 7.85-7.94 (m, 2H), 10.20 (br s, 1H). HRMS (M+H)$^+$ calcd for $C_{21}H_{24}N_5O_6S$ 474.1442, found 474.1479.

2-[4-(2,5-Dichloro-benzenesulfonyl)-piperazin-1-yl]-6,7-dimethoxy-quinazolin-4-ylamine (26): Compound 26 was synthesized from the procedure described for compound 11. $^1$HNMR (DMSO-d$_6$) δ 3.33 (br s, 4H), 3.64 (s, 3H), 3.78-3.82 (m, 4H), 3.82 (s, 3H), 6.74 (s, 1H), 7.21 (br s, 2H), 7.43 (s, 1H), 7.69-7.96 (m, 2H), 7.97 (s, 1H). HRMS (M+H)$^+$ calcd for $C_{20}H_{22}Cl_2N_5O_4S$ 498.0764, found 498.0768.

4-[4-(4-Amino-6,7-dimethoxy-quinazolin-2-yl)-piperazine-1-sulfonyl]-benzene-1,3-diamine (27): Compound 27 was synthesized from the procedure described for compound 11 following by hydrogenation to get diamine product. $^1$HNMR (DMSO-d$_6$) δ 3.09 (s, 4H), 3.34 (s, 3H), 3.67 (s, 3H), 3.86-3.89 (m, 4H), 6.28 (d, J=8.5 Hz, 1H), 6.74 (s, 1H), 7.31 (d, J=9.0 Hz, 1H), 7.66 (s, 1H), 8.23 (s, 1H), 8.64 (s, 1H), 8.85 (s, 1H), 8.99 (s, 1H). HRMS (M+H)$^+$ calcd for $C_{20}H_{26}N_7O_6S$ 460.1761, found 460.1758. Anal. ($C_{20}H_{25}N_7O_6S$·HCl) C, H, N.

5-[4-(4-Amino-6,7-dimethoxy-quinazolin-2-yl)-piperazine-1-sulfonyl]-2-chloro-4-fluoro-benzoic acid (28): Compound 28 was synthesized from the procedure described for compound 11. $^1$HNMR (DMSO-d$_6$) δ 3.15 (s, 4H), 3.70 (s, 3H), 3.76 (s, 3H), 3.80 (s, 4H), 6.76 (s, 1H), 7.37 (br s, 1H), 7.42 (s, 1H), 7.82 (s, 1H), 8.12 (s, 1H). HRMS (M+H)$^+$ calcd for $C_{21}H_{22}ClFN_5O_6S$ 526.0958, found 526.0943.

5-[4-(4-Amino-6,7-dimethoxy-quinazolin-2-yl)-piperazine-1-sulfonyl]-2,4-dichloro-benzoic acid (29): Compound 29 was synthesized from the procedure described for compound 11. $^1$HNMR (DMSO-d$_6$) δ 3.37 (br s, 4H), 3.81 (s, 3H), 3.85 (s, 3H), 3.95 (s, 4H), 7.47 (s, 1H), 7.71 (s, 2H), 7.43 (s, 1H), 8.03 (s, 1H), 8.33 (s, 1H), 8.62 (br s, 1H), 8.86 (br s, 1H). HRMS (M+H)$^+$ calcd for $C_{21}H_{22}Cl_2N_5O_6S$ 542.0662, found 542.0657.

6,7-Dimethoxy-2-[4-(naphthalene-1-sulfonyl)-piperazin-1-yl]-quinazolin-4-yl-amine (30): Compound 30 was synthesized from the procedure described for compound 11. $^1$HNMR (DMSO-d$_6$) δ 3.08 (s, 4H), 3.81 (s, 3H), 3.83 (s, 3H), 3.95 (s, 4H), 7.66 (s, 1H), 7.68-7.78 (m, 4H), 8.11 (d, J=8.0 Hz, 1H), 8.18 (d, J=7.4 Hz, 1H), 8.31 (d, J=8.2 Hz, 1H), 8.71 (d, J=8.6 Hz, 1H), 10.29 (br s, 2H). HRMS (M+H)$^+$ calcd for $C_{24}H_{26}N_5O_4S$ 480.1700, found 480.1696. Anal. ($C_{24}H_{25}N_5O_4S$·HCl) C, H, N.

6,7-Dimethoxy-2-[4-(naphthalene-2-sulfonyl)-piperazin-1-yl]-quinazolin-4-yl-amino (31): Compound 31 was synthesized from the procedure described for compound 11. $^1$HNMR (DMSO-d$_6$) δ 3.00-3.08 (m, 4H), 3.39 (s, 3H), 3.43 (s, 3H), 3.74-3.81 (m, 4H), 6.67 (s, 1 H), 7.12 (br s, 2H), 7.36 (s, 1H), 7.66-7.73 (m, 2H), 7.77 (d, J=8.7 Hz, 1H), 8.05 (d, J=7.7 Hz, 1 H), 8.14 (d, J=8.7 Hz, 1 H), 8.20 (d, J=7.7 Hz, 1 H), 8.45 (s, 1 H). HRMS (M+H)$^+$ calcd for $C_{24}H_{26}N_5O_4S$ 480.1700, found 480.1708. Anal. ($C_{24}H_{25}N_5O_4S$·HCl) C, H, N.

2-[4-(5-Dimethylamino-naphthalene-1-sulfonyl)-piperazin-1-yl]-6,7-dimethoxy-quinazolin-4-ylamine (32): Compound 32 was synthesized from the procedure described for compound 14. $^1$HNMR (DMSO-d$_6$) δ 2.82 (s, 6H), 3.27-3.29 (m, 4H), 3.44 (s, 3H), 3.81 (s, 3H), 3.85-3.91 (m, 4H), 7.27 (d, J=7.6 Hz, 1H), 7.61 (s, 1H), 7.61-7.70 (m, 3H), 8.17 (d, J=7.4 Hz, 1H), 8.35 (d, J=8.64 Hz, 1H), 8.53 (d, J=8.5 Hz, 1 H), 8.63 (br s, 1H), 8.85 (br s, 1H). HRMS (M+H)$^+$ calcd for $C_{26}H_{31}N_6O_4S$ 523.2122, found 523.2153.

2-[4-(Biphenyl-4-sulfonyl)-piperazin-1-yl]-6,7-dimethoxy-quinazolin-4-ylamine (33): Compound 33 was synthesized from the procedure described for compound 11. $^1$HNMR (DMSO-d$_6$) δ 3.02-3.03 (m, 4 H), 3.81 (s, 3 H), 3.86 (s, 3 H), 3.98-3.46 (m, 4 H), 7.38-7.52 (m, 4 H), 7.68-7.74 (m, 3 H), 7.85 (d, J=8.2 Hz, 2 H), 7.94 (d, J=8.2 Hz, 2 H). HRMS (M+H)$^+$ calcd for $C_{26}H_{28}N_5O_4S$ 506.1857, found 506.1840. Anal. ($C_{26}H_{27}N_5O_4S$·HCl) C, H, N.

6,7-Dimethoxy-2-[4-(2,4,6-triisopropyl-benzonesulfonyl)-piperazin-1-yl]-quinazolin-4-yl-amine (34): Compound 34 was synthesized from the procedure described for compound 11. $^1$HNMR (DMSO-d$_6$) δ 1.22 (s, 9H), 1.24 (s, 9H), 2.92-2.98 (m, 1H), 3.23 (s, 4H), 3.84 (s, 3H), 3.87 (s, 3H), 3.94 (s, 4H), 4.01-4.15 (m, 2H), 7.32 (s, 2H), 7.44 (s, 1H), 7.76 (s, 1H), 8.69 (br s, 1H), 8.96 (br s, 1H). HRMS (M+H)+ calcd for $C_{29}H_{42}N_5O_4S$ 556.2952, found 556.2944.

6,7-Dimethoxy-2-[4-(4'-methyl-biphenyl-4-sulfonyl)-piperazin-1-yl]-quinazolin-4-yl-amine (36): Compound 36 was synthesized from the procedure described for compound 35. $^1$HNMR (CD$_3$OD-d$_4$) δ 2.28 (s, 3H), 3.12 (s, 4H), 3.78 (s, 3H), 3.84 (s, 3H), 3.86 (s, 4H), 6.88-6.90 (m, 3H), 7.18 (d, J=8.1 Hz, 1H), 7.36 (s, 1H), 7.38-7.40 (m, 2H), 7.44 (d, J=8.1 Hz, 1H), 7.46-7.78 (m, 2H). HRMS (M+H)+ calcd for $C_{27}H_{30}N_5O_4S$ 520.2013, found 520.2040. Anal. ($C_{27}H_{29}N_5O_4S$·HCl) C, H, N.

6,7-Dimethoxy-2-[4-(4'-trifluoromethyl-biphenyl-4-sulfonyl)-piperazin-1-yl]-quinazolin-4-yl-amine (37): Compound 37 was synthesized from the procedure described for compound 35. $^1$HNMR (DMSO-d$_6$) δ 3.05 (s, 4H), 3.78 (s, 3H), 3.82 (s, 2H), 3.91 (s, 3H), 7.53 (s, 1H), 7.71-7.89 (m, 4H), 7.94-8.07 (m, 4H), 10.16 (s, 1H). HRMS (M+H)+ calcd for $C_{27}H_{26}F_3N_5O_4S$ 574.1730, found 574.1728. Anal. ($C_{27}H_{25}F_3N_5O_4S$·HCl) C, H, N.

2-[4-(4'-Methanesulfonyl-biphenyl-4-sulfonyl)-piperazin-1-yl]-6,7-dimethoxy-quinazolin-4-ylamine (38): Compound 38 was synthesized from the procedure described for compound 35. $^1$HNMR (DMSO-d$_6$) δ 2.91 (s, 4H), 3.26 (s, 3H), 3.78 (s, 2H), 3.83 (s, 3H), 3.91 (s, 4H), 6.97 (s, 1H), 7.55 (s, 1H), 7.88 (d, J=8.2 Hz, 2H), 8.08 (m, 6H). HRMS (M+H)+ calcd for $C_{27}H_{30}N_5O_6S_2$ 584.1632, found 584.1658. Anal. ($C_{27}H_{29}N_5O_6S_2$·HCl) C, H, N.

2-[4-(4'-Butyl-biphenyl-4-sulfonyl)-piperazin-1-yl]-6,7-dimethoxy-quinazolin-4-yl-amine (39): Compound 39 was synthesized from the procedure described for compound 35. $^1$HNMR (DMSO-d$_6$) δ 0.89 (t, J=7.3 Hz, 3H), 1.29-1.34 (m, 2H), 1.55-1.59 (m, 2H), 2.60-2.64 (m, 2H), 3.13 (s, 4H), 3.81 (s, 3H), 3.86 (s, 3H), 3.97 (s, 4H), 7.31-7.33 (m, 3H), 7.63-7.69 (m, 3H), 7.82 (d, J=8.3 Hz, 2H), 7.91 (d, J=8.4 Hz, 2H), 8.66 (br s, 1H), 8.79 (br s, 1H). HRMS (M+H)+ calcd for $C_{30}H_{36}N_5O_4S$ 562.2483, found 562.2458. Anal. ($C_{30}H_{35}N_5O_4S$·HCl) C, H, N.

2-[4-(4'-tert-Butyl-biphenyl-4-sulfonyl)-piperazin-1-yl]-6,7-dimethoxy-quinazolin-4-yl-amine (40): Compound 40 was synthesized from the procedure described for compound 35. $^1$HNMR (DMSO-d$_6$) δ 1.31 (s, 9H), 3.14 (s, 4H), 3.81 (s, 3H), 3.86 (s, 3H), 3.95 (s, 4H), 7.19 (s, 1H), 7.45-7.53 (m, 2H), 7.60-7.66 (m, 3H), 7.82-7.84 (m, 2H), 7.92 (d, J=8.3 Hz, 2H), 8.66 (br s, 1H), 8.81 (br s, 1H). HRMS (M+H)+ calcd for $C_{30}H_{36}N_5O_4S$ 562.2483, found 562.2471. Anal. ($C_{30}H_{35}N_5O_4S$·HCl) C, H, N.

N-[2-(4-Amino-6,7-dimethoxy-quinazolin-2-ylamino)-ethyl]-4-biphenylsulfonamide (42): Compound 42 was synthesized from the procedure described for compound 41. $^1$HNMR (DMSO-d$_6$) δ 3.05 (s, 2H), 3.46 (s, 2H), 3.80 (s, 3H), 3.83 (s, 3H), 6.91 (br s, NH), 7.40-7.47 (m, 3H), 7.60-7.64 (m, 3H), 7.78-7.83 (m, 2H), 7.86-7.88 (m; 2H), 8.01 (s, 1H). HRMS (M+H)+ calcd for $C_{24}H_{26}N_5O_4S$ 480.1700, found 480.1687. Anal. ($C_{24}H_{25}N_5O_4S$·HCl) C, H, N.

2-[4-(Biphenyl-4-sulfonyl)-piperazin-1-yl]-6,7-dipropoxy-quinazolin-4-yl-amine (44): Compound 44 was synthesized from the procedure described for compound 43. $^1$HNMR (DMSO-d$_6$) δ 0.99 (t, J=7.3 Hz, 6H), 1.71-1.83 (m, 4 H), 3.12 (br s, 4 H), 3.93-4.14 (m, 8 H), 7.33 (s, 1 H), 7.44-7.54 (m, 3 H), 7.65 (s, 1 H), 7.75-7.79 (m, 2 H), 7.86 (d, J=8.3 Hz, 2 H), 7.94 (d, J=8.3 Hz, 2 H). HRMS (M+H)+ calcd for $C_{30}H_{36}N_5O_4S$ 562.2483, found 562.2466. Anal. ($C_{30}H_{35}N_5O_4S$·HCl) C, H, N.

2-[4-(Biphenyl-4-sulfonyl)-piperazin-1-yl]-6,7-diisopropoxy-quinazolin-4-yl-amine (45): Compound 45 was synthesized from the procedure described for compound 43. $^1$HNMR (DMSO-d$_6$) δ 1.25 (s, 3 H), 1.27 (s, 3 H), 1.33 (s, 3 H), 1.35 (s, 3 H), 3.12 (br s, 4 H), 3.96 (br s, 4 H), 4.41-4.66 (m, 2 H), 7.36 (s, 1 H), 7.41-7.53 (m, 3 H), 7.68-7.84 (m, 3 H), 7.83-7.86 (m, 4 H), 8.59 (br s, NH), 8.76 (br s, NH). HRMS (M+H)+ calcd for $C_{30}H_{36}N_5O_4S$ 562.2483, found 562.2478. Anal. ($C_{30}H_{35}N_5O_4S$·HCl) C, H, N.

2-[4-(Biphenyl-4-sulfonyl)-piperazin-1-yl]-6,7-dibutoxy-quinazolin-4-ylamine (46): Compound 46 was synthesized from the procedure described for compound 43. $^1$HNMR (DMSO-d$_6$) δ 0.934 (t, J=7.5 Hz, 6 H), 1.44 (q, J=7.5 Hz, 4 H), 1.66-1.812 (m, 4 H), 3.13 (br s, 4 H), 3.91 (br s, 4 H), 3.91-4.08 (m, 4 H), 7.21 (s, 1 H), 7.41-7.53 (m, 3 H), 7.64 (s, 1 H), 7.73 (d, J=8.0 Hz, 1 H), 7.74 (s, 1 H), 7.829-7.864 (m, 3 H), 7.94 (d, J=8.0 Hz, 2 H). HRMS (M+H)+ calcd for $C_{32}H_{40}N_5O_4S$ 590.2795, found 590.2770. Anal. ($C_{32}H_{39}N_5O_4S$·HCl) C, H, N.

Example 3

Testing of Compounds, and Results

All compounds were evaluated for their ability to induce apoptotic death in human androgen-independent PC-3 prostate cancer in RPMI 1640 medium containing 10% fetal bovine serum (FBS). For representative compounds tested in DU-145 and LNCaP prostate cancer cells, the IC$_{50}$ values for inhibiting cell proliferation were similar in these three cell lines irrespective of differences in androgen sensitivity, PTEN mutation, the functional status of p53 and Rb, and other biomarkers.

Role of the aromatic acyl-side chains in apoptosis induction (Strategy A). Substitution of the 2,3-dihydro-benzo[1,4]dioxane moiety of doxazosin with different aromatic acyl-side chains gave derivatives with varying potency in apoptosis induction (Table 1). In general, analogues with hydrophilic side chains exhibited lower apoptosis-inducing activity, while that of a hydrophobic aromatic system, e.g., t-butylphenyl, retained the in vitro efficacy. These findings, however, provided a proof of principle that doxazosin was amenable to structural optimization to develop a new class of apoptosis-inducing agents.

TABLE 1

Structures and IC$_{50}$ values of compounds 1-10.

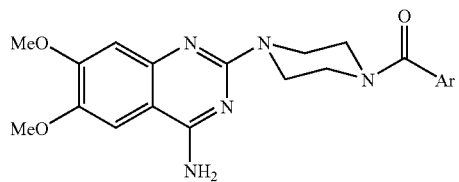

| Entry | Ar | IC$_{50}$* (PC-3) |
|---|---|---|
| Doxazosin | 2,3-dihydro-benzo[1,4]dioxane | 45 ± 5 |
| 1 | 4-Chlorophenyl | 60 ± 8 |
| 2 | 4-Cyanophenyl | 68 ± 6 |
| 3 | Benzyloxy | 63 ± 6 |
| 4 | 3-Cyanophenyl | 82 ± 5 |
| 5 | 4-Nitrophenyl | 75 ± 11 |
| 6 | 3,4-Dimethoxyphenyl | 71 ± 8 |
| 7 | 1-Naphthyl | 59 ± 4 |
| 8 | 4-Aminophenyl | >100 |
| 9 | 4-t-Butylphenyl | 47 ± 6 |
| 10 | 4-(Trifluoromethyl)phenyl | >100 |

TABLE 1-continued

Structures and IC$_{50}$ values of compounds 1-10.

| Entry | Ar | IC$_{50}$* (PC-3) |
|---|---|---|

*Values represent means ± S.D. (n = 6).

Aryl sulfonamide derivatives exhibited high potency in triggering apoptosis (Strategy B). To further explore the functional role of the acyl function in apoptosis induction, the carboxamide moiety of compounds 1, 5, 7, and 9 was replaced with sulfonamide, yielding compounds 11, 17, 30, and 23, respectively. As shown in Table 2, this substitution resulted in a substantial increase in apoptosis-inducing potency.

TABLE 2

Structures and IC50 values of compounds 11-35.

| Entry | Ar | IC$_{50}$ (PC-3) |
|---|---|---|
| 11 | 4-Chlorophenyl | 23 ± 3 |
| 12 | 4-Bromophenyl | 20 ± 2 |
| 13 | 4-Iodophenyl | 15 ± 2 |
| 14 | 5-Chlorothienyl | 25 ± 3 |
| 15 | 2-Nitrophenyl | 35 ± 4 |
| 16 | 3-Nitrophenyl | 32 ± 5 |
| 17 | 4-Nitrophenyl | 36 ± 3 |
| 18 | 4-Methylphenyl | 30 ± 2 |
| 19 | 4-(Trifluoromethyl)-phenyl | 27 ± 3 |
| 20 | 4-Methoxyphenyl | 39 ± 4 |
| 21 | 4-(Trifluoromethoxy)-phenyl | 25 ± 2 |
| 22 | 4-(Methylsulfonyl)-phenyl | 17 ± 3 |
| 23 | 4-t-Butylphenyl | 4.1 ± 0.7 |
| 24 | 3-Carboxyphenyl | 53 ± 4 |
| 25 | 4-Carboxyphenyl | 53 ± 5 |
| 26 | 2,5-Dichlorophenyl | 60 ± 7 |
| 27 | 2,4-Diaminophenyl | 67 ± 5 |
| 28 | 3-Carboxy-4-chloro-5-fluorophenyl | 56 ± 4 |
| 29 | 3-Carboxy-4,6-dichloro-phenyl | 52 ± 6 |
| 30 | 1-Naphthyl | 14 ± 2 |
| 31 | 2-Naphthyl | 15 ± 2 |
| 32 | 1-(5-Dimethylamino)-naphthyl | 29 ± 4 |
| 33 | Biphenyl | 4.2 ± 0.8 |
| 34 | 2,4,6-Tri-isopropyl-phenyl | 24 ± 3 |
| 35 | 4-(Phenanthren-9-yl)phenyl | 5.2 ± 0.9 |

*Values represent means ± S.D. (n = 6).

Figure 5:
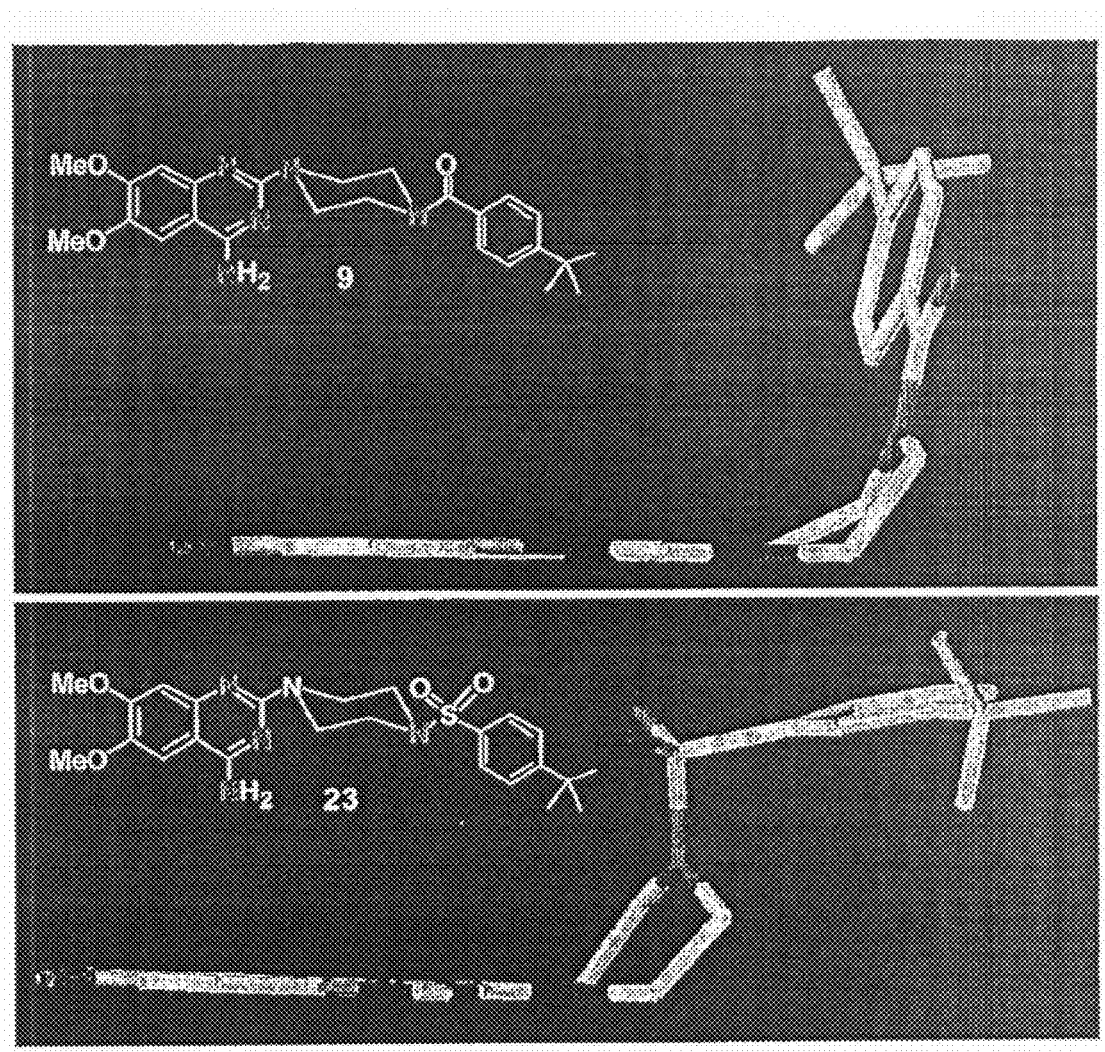
FIG. 5 shows a comparison of chemical and 3D structures of compounds 9 and 23. The 3D structures of small molecules were generated using the software SYBYL 6.9 (Tripos Associate; St. Louis, Mo.) on Silicon Graphics O2 (Silicon Graphics Inc.; Mountain View, Calif.). Energy minimization was carried out with default parameters (minimum RMS gradient, 0.005 kcal/mol; maximum iterations, 1,000; minimum energy change, 0.05 kcal/mol).

Among these four pairs of compounds, 23 exhibited an-order-of-magnitude higher potency than its carboxamide counterpart 9. To understand the structural basis for this improvement in potency, the energy-minimized structures of compounds 9 and 23 were compared (FIG. 5).

As shown, the core structural component, i.e., the quinazoline base and the adjacent piperazine ring, conferred a high degree of structural rigidity to the molecule. The boat conformation of the piperazine ring oriented the $N^1$ appendage, i.e., carbonyl or sulfonyl, perpendicular to the quinazoline-planar structure. The discrepancy in potency was believed to be was attributable to the transition from a trigonal planar structure of a carboxamide moiety (upper panel) to a tetrahedron-like structure of sulfonamide (lower panel). As a result, the spatial arrangement of the aromatic side arm relative to the neighboring plane of the quinazoline system differed.

Further examinations of the impact of the aryl sulfonamide function on apoptosis-inducing potency confirmed the preference for bulky, hydrophobic aromatic systems (Table 2). Among the 25 derivatives examined, compounds 23, 33 and 35, with the side chains of t-butylphenyl, biphenyl, and phenanthren-9-yl-phenyl, respectively, represented the optimal compounds, with IC$_{50}$ values in the range of 4-5 µM in 10% serum-containing medium at 48 h.

Figure 6:
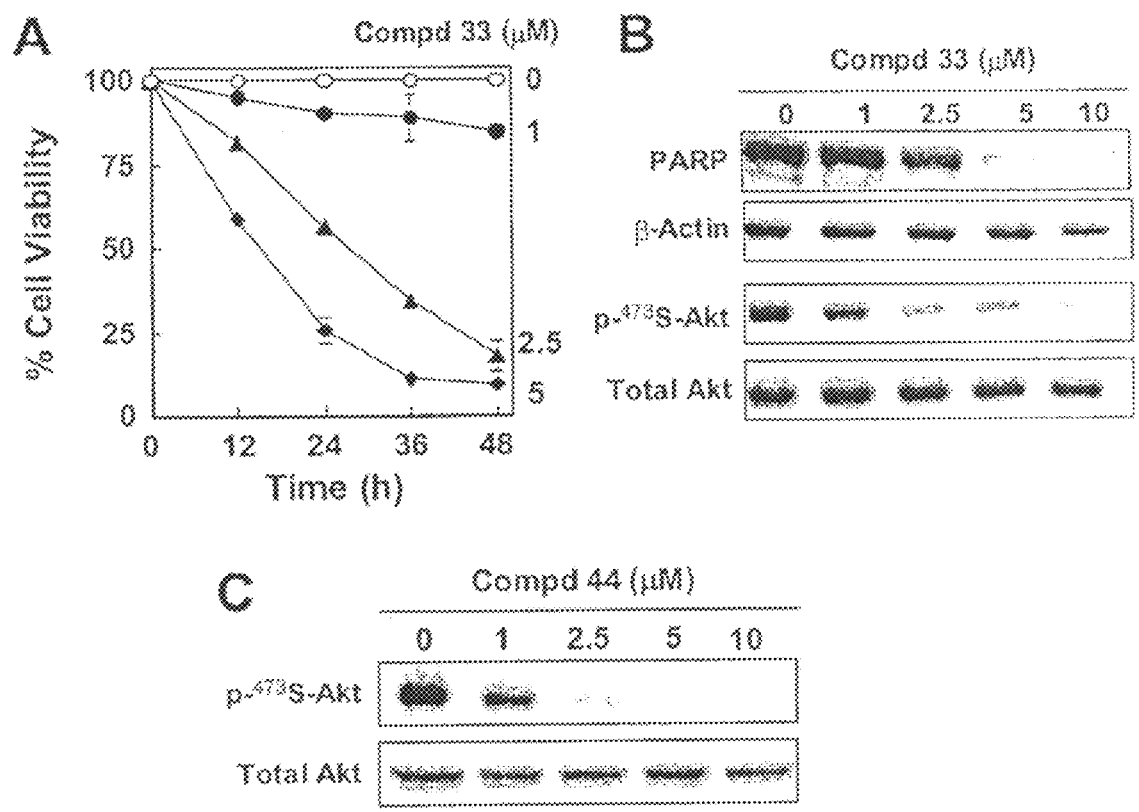
FIG. 6 shows (A) Time- and dose-dependent effects of compound 33 on the cell viability of PC-3 cells in 1% FBS-supplemented RPMI 1640 medium. (B) Western blot analysis of RAPR proteolysis and Akt dephosphorylation in PC-3 cells treated with the indicated concentrations of 33 for 48 h. (C) Effects of compound 44 on Akt phosphorylation in PC-3 cells treated with the indicated concentrations for 48 h.

FIG. 6A shows a dose-dependent effect of compound 33 on apoptosis in 1% FBS-supplemented medium, as evidenced by PARP proteolysis (FIG. 6B), with IC$_{50}$ of approximately 2.5 µM at 48 h. Western blot analysis confirmed that this apoptotic effect was attributable, in part, to the inhibition of Akt activation (FIG. 6B).

Further modifications of the biphenyl ring of compound 33 by adding alkyl chains such as $CH_3$, $CF_3$, or $n-C_4H_9$ at the 4' position did not further improve the apoptosis-inducing potency (Table 3). However, a significant drop in potency was noted with the bulky t-butyl substitution.

TABLE 3

Structures and IC$_{50}$ values of compounds 36-40.

| Entry | R | IC$_{50}$ (PC-3) |
|---|---|---|
| 36 | 4-Methyl | 3.4 ± 0.4 |
| 37 | 4-Trifluoromethyl | 3.3 ± 0.3 |
| 38 | 4-Methylsulfonyl | 7.2 ± 0.5 |
| 39 | 4-n-Butyl | 3.4 ± 0.2 |
| 40 | 4-t-Butyl | 10 ± 2 |

*Values represent means ± S.D. (n = 6).

The piperazine ring is important to the apoptosis-inducing potency (Strategy C). The 4-(4-amino-6,7-dimethoxy-quinaolin-2-yl)-piperazine moiety provided structural rigidity to the molecule, which might play a role in the ligand-protein interactions. To examine this premise, the piperazine ring of compounds 23 and 33 was replaced with an ethylenediamine linker, generating 41 and 42 (Chart 1)

Chart 1. Structures and IC$_{50}$ Values of Compounds 41 and 42.

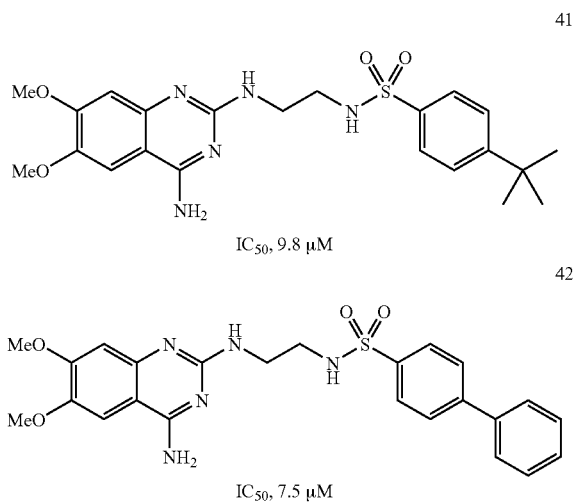

41

IC$_{50}$, 9.8 μM

42

IC$_{50}$, 7.5 μM

This replacement resulted in a twofold decrease in apoptosis-inducing potency, suggesting the importance of this unique structural feature in maintaining the efficacy.

Role of the alkoxy substituent on the quinazoline ring in the induction of apoptosis (Strategy D). To further optimize the activity of compound 33 in inducing apoptosis, we replaced the methoxy side chains with alkoxy functions with different stereochemical properties (Table 4).

TABLE 4

Structures and IC$_{50}$ values of compounds 43-46.

| Entry | R | IC$_{50}$ (PC-3) |
|---|---|---|
| 43 | Allyl | 3.3 ± 0.4 |
| 44 | n-Propyl | 2.5 ± 0.3 |
| 45 | Isopropyl | 24 ± 5 |
| 46 | n-Butyl | 3.5 ± 0.4 |

*Values represent means ± S.D. (n = 6).

Among the four derivatives, compound 44 represented the optimal compound with slight improvement in potency (IC$_{50}$, 2.5 μM in 10% FBS-supplemented medium), while its isopropyl counterpart 45 displayed a precipitous drop in potency (IC$_{50}$, 24 μM). These data suggest a very subtle impact of the quinazoline side chain structure on target binding. Again, the induction, of apoptosis by compound 44 is characterized by the dephosphorylation of phospho-Akt in a dose-dependent manner, which was evident as low as 1 μM (FIG. 6C).

Discussion

Several lines of evidence that doxazosin mediated apoptosis, in part, through the down-regulation of Akt signaling in PC-3 cells have now been obtained and described herein. As Akt plays a pivotal role in regulating cell growth and survival in cancer cells, this finding underpins the pharmacological exploitation of doxazosin to develop a novel class of apoptosis-inducing agents that block intracellular Akt activation. However, the target whereby doxazosin and the present inventive compounds mediate Akt down-regulation is still under investigation.

Kinase assay data indicate that these agents displayed no direct inhibition in vitro on protein kinase C isozymes, or any of the upstream kinases of Akt including phosphoinositide-dependent kinase-1 and phosphoinositide 3-kinase (data not shown). It is plausible that these quinazoline-based derivatives, through competing with ATP binding, interfere with a yet unidentified tyrosine kinase that uses Akt, but not ERKs, as a downstream effector. It is noteworthy that the present agents are structurally distinct from existing quinazoline-based inhibitors of epidermal growth receptor tyrosine kinases[18] such as Iressa (ZD1839) and CP-358,744.

Replacement of the (2,3-dihydro-benzo[1,4]dioxane)-carbonyl moiety of doxazosin with aryl sulfonyl substituents dramatically improved the potency in facilitating Akt dephosphorylation and inducing apoptosis. The structurally optimized agent 33 exhibited an order-of-magnitude higher potency than doxazosin in triggering apoptotic death in PC-3 cells. It is noteworthy that the structural rigidity incurred by the piperazine linker was integral to maintaining the high potency of these derivatives. Consequently, use of a flexible linker such as ethylenediamine substantially reduced the apoptosis-inducing activity of 33.

Further structural improvement was accomplished by replacing the methoxy side chains on the quinazoline ring with propoxy functions. Both 33 and 44 were effective in suppressing the proliferation of different prostate cancer cell lines at low μM levels. In addition, both agents were submitted to the Developmental Therapeutic Program (DTP) at the National Cancer Institute (NCI) for screening against sixty human tumor cells lines, representing leukemia, melanoma, and cancers of lung, colon, brain, ovary, breast, prostate, and kidney. Table 5 is a list of the cell lines tested in the DTP Screening program.

TABLE 5

| Cell Line Name | Panel Name | Doubling Time | Inoculation Density |
|---|---|---|---|
| CCRF-CEM | Leukemia | 26.7 | 40000 |
| HL-60(TB) | Leukemia | 28.6 | 40000 |
| K-562 | Leukemia | 19.6 | 5000 |
| MOLT-4 | Leukemia | 27.9 | 30000 |
| RPMI-8226 | Leukemia | 33.5 | 20000 |
| SR | Leukemia | 28.7 | 20000 |
| A549/ATCC | Non-Small Cell Lung | 22.9 | 7500 |
| EKVX | Non-Small Cell Lung | 43.6 | 20000 |
| HOP-62 | Non-Small Cell Lung | 39 | 10000 |
| HOP-92 | Non-Small Cell Lung | 79.5 | 20000 |
| NCI-H226 | Non-Small Cell Lung | 61 | 20000 |
| NCI-H23 | Non-Small Cell Lung | 33.4 | 20000 |
| NCI-H322M | Non-Small Cell Lung | 35.3 | 20000 |
| NCI-H460 | Non-Small Cell Lung | 17.8 | 7500 |
| NCI-H522 | Non-Small Cell Lung | 38.2 | 20000 |
| COLO 205 | Colon | 23.8 | 15000 |
| HCC-2998 | Colon | 31.5 | 15000 |
| HCT-116 | Colon | 17.4 | 5000 |
| HCT-15 | Colon | 20.6 | 10000 |
| HT29 | Colon | 19.5 | 5000 |
| KM12 | Colon | 23.7 | 15000 |
| SW-620 | Colon | 20.4 | 10000 |
| SF-268 | CNS | 33.1 | 15000 |
| SF-295 | CNS | 29.5 | 10000 |
| SF-539 | CNS | 35.4 | 15000 |
| SNB-19 | CNS | 34.6 | 15000 |
| SNB-75 | CNS | 62.8 | 20000 |
| U251 | CNS | 23.8 | 7500 |

TABLE 5-continued

| Cell Line Name | Panel Name | Doubling Time | Inoculation Density |
|---|---|---|---|
| LOX IMVI | Melanoma | 20.5 | 7500 |
| MALME-3M | Melanoma | 46.2 | 20000 |
| M14 | Melanoma | 26.3 | 15000 |
| SK-MEL-2 | Melanoma | 45.5 | 20000 |
| SK-MEL-28 | Melanoma | 35.1 | 10000 |
| SK-MEL-5 | Melanoma | 25.2 | 10000 |
| UACC-257 | Melanoma | 38.5 | 20000 |
| UACC-62 | Melanoma | 31.3 | 10000 |
| IGR-OV1 Restricted Use | Ovarian | 31 | 10000 |
| OVCAR-3 | Ovarian | 34.7 | 10000 |
| OVCAR-4 | Ovarian | 41.4 | 15000 |
| OVCAR-5 | Ovarian | 48.8 | 20000 |
| OVCAR-8 | Ovarian | 26.1 | 10000 |
| SK-OV-3 | Ovarian | 48.7 | 20000 |
| 786-0 | Renal | 22.4 | 10000 |
| A498 | Renal | 66.8 | 25000 |
| ACHN | Renal | 27.5 | 10000 |
| CAKI-1 | Renal | 39 | 10000 |
| RXF 393 Restricted Use | Renal | 62.9 | 15000 |
| SN12C | Renal | 29.5 | 15000 |
| TK-10 Restricted Use | Renal | 51.3 | 15000 |
| UO-31 | Renal | 41.7 | 15000 |
| PC-3 | Prostate | 27.1 | 7500 |
| DU-145 | Prostate | 32.3 | 10000 |
| MCF7 | Breast | 25.4 | 10000 |
| NCI/ADR-RES | Breast | 34 | 15000 |
| MDA-MB-231/ATCC | Breast | 41.9 | 20000 |
| HS 578T | Breast | 53.8 | 20000 |
| MDA-MB-435 | Breast | 25.8 | 15000 |
| MDA-N Not Available | Breast | 22.5 | 15000 |
| BT-549 | Breast | 53.9 | 20000 |
| T-47D Restricted Use | Breast | 45.5 | 20000 |

All the tested cell lines showed high degree of sensitivity to the growth inhibitory effects of 33 and 44. The mean $GI_{50}$ values (concentration resulting in 50% growth inhibition) among these sixty cell lines were 2.2 and 1.5 µM, respectively. These data clearly demonstrate the in vitro efficacy of these agents, and their potential application in cancer prevention and/or treatment.

Other embodiments of the invention will be apparent to those skilled in the art from consideration of the specification and practice of the invention disclosed herein. It is intended that the specification and examples be considered as exemplary only, with a true scope and spirit of the invention being indicated by the claims.

Cited Documents (1) Kirby, R. S.; Pool, J. L. Alpha adrenoceptor blockade in the treatment of benign prostatic hyperplasia: past, present and future. *Br J Urol* 1997, 80, 521-532.
(2) Kyprianou, N.; Jacobs, S. C. Induction of apoptosis in the prostate by alpha1-adrenoceptor antagonists: a novel effect of "old" drugs. *Curr Urol Rep* 2000, 1, 89-96.
(3) Kyprianou, N.; Benning, C. M. Suppression of human prostate cancer cell growth by alpha1-adrenoceptor antagonists doxazosin and terazosin via induction of apoptosis. *Cancer Res* 2000, 60, 4550-4555.
(4) Kyprianou, N.; Chon, J.; Benning, C. M. Effects of alpha (1)-adrenoceptor (alpha(1)-AR) antagonists on cell proliferation and apoptosis in the prostate: therapeutic implications in prostatic disease. *Prostate Suppl* 2000, 9, 42-46.
(5) Kyprianou, N. Doxazosin and terazosin suppress prostate growth by inducing apoptosis: clinical significance. *J Urol* 2003, 169, 1520-1525.
(6) Cuellar, D. C.; Rhee, J.; Kyprianou, N. Alpha1-adrenoceptor antagonists radiosensitize prostate cancer cells via apoptosis induction. *Anticancer Res* 2002, 22, 1673-1679.
(7) Cal, C.; Uslu, R.; Gunaydin, G.; Ozyurt, C.; Omay, S. B. Doxazosin: a new cytotoxic agent for prostate cancer? *BJU Int* 2000, 85, 672-675.
(8) Anglin, I. E.; Glassman, D. T.; Kyprianou, N. Induction of prostate apoptosis by alpha1-adrenoceptor antagonists: mechanistic significance of the quinazoline component. *Prostate Cancer Prostatic Dis* 2002, 5, 88-95.
(9) Benning, C. M.; Kyprianou, N. Quinazoline-derived alpha1-adrenoceptor antagonists induce prostate cancer cell apoptosis via an alpha1-adrenoceptor-independent action. *Cancer Res* 2002, 62, 597-602.
(10) Ilio, K. Y.; Park, I I; Pins, M. R.; Kozlowski, J. M.; Lee, C. Apoptotic activity of doxazosin on prostate stroma in vitro is mediated through an autocrine expression of TGF-beta1. *Prostate* 2001, 48, 131-135.
(11) Partin, J. V.; Anglin, I. E.; Kyprianou, N. Quinazoline-based alpha 1-adrenoceptor antagonists induce prostate cancer cell apoptosis via TGF-beta signalling and I kappa B alpha induction. *Br J Cancer* 2003, 88, 1615-1621.
(12) Datta, S. R.; Brunet, A.; Greenberg, M. E. Cellular survival: a play in three Akts. *Genes Dev* 1999, 13, 2905-2927.
(13) Bonni, A.; Brunet, A.; West, A. E.; Datta, S. R.; Takasu, M. A. et al. Cell survival promoted by the Ras-MAPK signaling pathway by transcription-dependent and -independent mechanisms. *Science* 1999, 286, 1358-1362.
(14) Meier, R.; Thelen, M.; Hemmings, B. A. Inactivation and dephosphorylation of protein kinase Balpha (PKBalpha) promoted by hyperosmotic stress. *Embo J* 1998, 17, 7294-7303.
(15) Kulp, S. K.; Yang, Y. T.; Hung, C. C.; Chen, K. F.; Lai, J. P. et al. 3-phosphoinositide-dependent protein kinase-1/Akt signaling represents a major cyclooxygenase-2-independent target for celecoxib in prostate cancer cells. *Cancer Res* 2004, 64, 1444-1451.
(16) Elliott, H. L.; Meredith, P. A.; Reid, J. L. Pharmacokinetic overview of doxazosin. *Am J Cardiol* 1987, 59, 78G-81G.
(17) Yang, C. C.; Lin, H. P.; Chen, C. S.; Yang, Y. T.; Tseng, P. H. et al. Bcl-xL mediates a survival mechanism independent of the phosphoinositide 3-kinase/Akt pathway in prostate cancer cells. *J Biol Chem* 2003, 278, 25872-25878.
(18) Fry, D. W. Inhibition of the epidermal growth factor receptor family of tyrosine kinases as an approach to cancer chemotherapy: progression from reversible to irreversible inhibitors. *Pharmacol Ther* 1999, 82, 207-218.

What is claimed is:
1. A compound having the following formula:

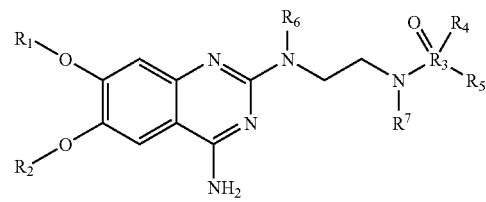

wherein:
  $R_1$ and $R_2$ are the same or different and are chosen from H, alkyl, and alkenyl;
  $R_3$ is S and $R_4$ is =O;

$R_5$ comprises an aryl group chosen from furyl, pyrrolyl, pyridyl, thiazolyl, oxazolyl, isoxazolyl, imidazolyl, pyrazolyl, pyrimidinyl, thiadiazolyl, oxadiazolyl, quinolyl, isoquinolyl, naphthyl, and phenyl, any of which may be substituted or unsubstituted; and $R_6$ and $R_7$ are i) the same or different and chosen from, H, alkyl, and alkenyl, or are ii) both —$CH_2$— and are bonded together to form a piperazinyl ring;

with the proviso that if $R_1$ and $R_2$ are both methyl, $R_3$ is C, and $R_6$ and $R_7$ are both —$CH_2$— and are bonded together to form a piperazinyl ring, then $R_5$ is not 2,3-dihydro-benzo[1,4]dioxane.

2. The compound according to claim 1, wherein $R_6$ and $R_7$ are both —$CH_2$— and are bonded together to form a piperazinyl ring.

3. The compound according to claim 2, wherein $R_1$ and $R_2$ are the same and are alkyl groups.

4. The compound according to claim 3, wherein the alkyl groups are methyl groups.

5. The compound according to claim 3, wherein $R_5$ is chosen from 2,3-dihydrobenzo[1,4]dioxane, 4-chlorophenyl, 4-cyanophenyl, benzyloxy, 3-cyanophenyl, 4-nitrophenyl, 3,4-dimethoxyphenyl, 1-naphthyl, 4-aminophenyl, 4-t-butylphenyl, and 4-(trifluoromethyl)phenyl.

6. The compound according to claim 1, wherein $R_5$ is chosen from 4-chlorophenyl, 4-bromophenyl, 4-iodophenyl, 5-chlorothienyl, 2-nitrophenyl, 3-nitrophenyl, 4-nitrophenyl, 4-methylphenyl, 4-(trifluoromethyl)-phenyl, 4-methoxyphenyl, 4-(trifluoromethoxy)-phenyl, 4-(methylsulfonyl)-phenyl, 4-t-butylphenyl, 3-carboxyphenyl, 4-carboxyphenyl, 2,5-dichlorophenyl, 2,4-diaminophenyl, 3-carboxy-4-chloro-5-fluorophenyl, 3-carboxy-4,6-dichloro-phenyl, 1-naphthyl, 2-naphthyl, 1-(5-dimethylamino)-naphthyl, biphenyl, 2,4,6-tri-isopropyl-phenyl, and 4-(phenanthren-9-yl)phenyl.

7. The compound according to claim 1, wherein $R_5$ comprises a substituted or unsubstituted biphenyl.

8. The compound according to claim 7, wherein $R_5$ is chosen from 4'-methyl-biphenyl, 4'-trifluoromethyl-biphenyl, 4'-methylsulfonyl-biphenyl, 4'-n-butyl-biphenyl, and 4'-t-butyl-biphenyl.

9. The compound according to claim 1, wherein $R_5$ is an unsubstituted biphenyl.

10. The compound according to claim 9, wherein $R_1$ and $R_2$ comprise groups chosen from methyl, ethyl, propyl, butyl, methylene, ethylene, propylene, and butylene.

11. The compound according to claim 10, wherein $R_1$ and $R_2$ are the same and are chosen from allyl, n-propyl, isopropyl, and n-butyl.

12. The compound according to claim 1, wherein $R_6$ and $R_7$ are H.

13. The compound according to claim 12, wherein $R_1$ and $R_2$ are the same and are alkyl groups.

14. The compound according to claim 13, wherein the alkyl groups are methyl groups.

15. The compound according to claim 14, wherein $R_5$ is chosen from 4-t-butyl-benzene and biphenyl.

16. The compound according to claim 1, wherein the compound is an ester or salt.

17. A compound having the following formula:

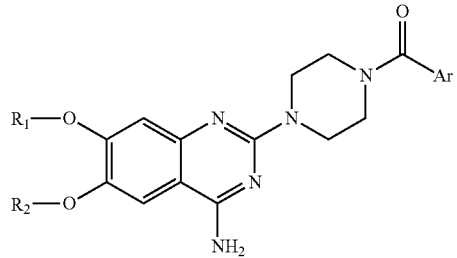

wherein:
$R_1$ and $R_2$ are the same or different and are chosen from H, alkyl, and alkenyl; and
Ar comprises an aryl group chosen from phenyl, naphthyl, biphenyl, and phenanthrenyl, any of which may be substituted or unsubstituted.

18. The compound of claim 17, wherein Ar is a substituted or unsubstituted biphenyl group.

19. The compound of claim 17, wherein $R_1$ and $R_2$ are allyl, n-propyl, or n-butyl.

20. A pharmaceutical composition comprising the compound according to claim 1, and at least one pharmaceutically acceptable excipient.

21. A method of inhibiting neoplastic cell proliferation in an animal having a cancer selected from the group consisting of prostate cancer, lung cancer, acute leukemia, multiple myeloma, bladder carcinoma, renal carcinoma, breast carcinoma, colorectal carcinoma, neuroblastoma, brain cancer, ovarian cancer, and melanoma, comprising administering a therapeutically effective amount of at least one compound according to claim 1.

22. The method according to claim 21, wherein the animal is a human.

* * * * *